United States Patent [19]
Johs et al.

[11] Patent Number: 5,936,734
[45] Date of Patent: Aug. 10, 1999

[54] ANALYSIS OF PARTIALLY POLARIZED ELECTROMAGNETIC RADIATION IN ELLIPSOMETER AND POLARIMETER SYSTEMS

[75] Inventors: Blaine D. Johs; Craig M. Herzinger, both of Lincoln, Nebr.

[73] Assignee: J.A. Woollam Co. Inc., Lincoln, Nebr.

[21] Appl. No.: 08/997,312

[22] Filed: Dec. 23, 1997

[51] Int. Cl.$^6$ .................................................. G01N 21/21
[52] U.S. Cl. .......................................... 356/364; 356/369
[58] Field of Search ................................... 356/364–369, 356/381, 382; 250/225

[56] References Cited

U.S. PATENT DOCUMENTS

| | | |
|---|---|---|
| 5,373,359 | 12/1994 | Woollam et al. . |
| 5,416,588 | 5/1995 | Ducharme et al. . |
| 5,504,582 | 4/1996 | Johs et al. . |
| 5,521,706 | 5/1996 | Green et al. . |

OTHER PUBLICATIONS

Multiwavelength Ellipsometry for Real Time Process Control . . . Maynard et al., J. Vac. Sci. Technol., B, 15(1) Jan./Feb. 1997.

In Sito Ellipsometry And Reflectometry During Etching . . . Haverlag et al., J. Vac. Sci. Technol. B 10(6) Nov./Dec. 1992.

Ultraviolet–Visible Ellipsometry for Process Control . . . Blayo et al., J. Opt. Sci. Am. A., vol. 12, No. 3, Mar. 1995.

In Situ And Ex Situ Application of Spectroscopic Ellipsometry Woollam et al., Mat. Research, Soc. Proc., vol. 324, 1994.

Thin–Film Interferometry of Patterned Films, Maynard et al., J. Vac. Sci. Technol. B, vol. 13, May/Jun. 1995.

Optical Etch–Rate Monitoring: Computer Simulation . . . Heimann et al., J. Electrochem. Soc., vol. 131, No. 4, Apr. 1984.

Optical Etch–Rate Using Active Device Areas: Lateral . . . Heimann, J. Electrochem. Soc., vol. 1–32, No. 8, Aug. 1985.

Spectral Ellipsometry On Patterned Wafers, Duncan, SPIE, vol. 2637, Apr. 1995.

Optical Analysis of Complex Multilayer Structures . . . Johs et. al., SPIE, vol. 2253, 1994.

Sample Depolarization Effects From Thin Film of ZnS . . . , Appl.Phys. Lett. 61(5), Aug. (1992).

The Accurate Determination of Optical Properties by Ellipsometry, Aspnes, Handbooks of Optical Constants, Academic Press, Palik Editor, 1985.

*Primary Examiner*—Hoa Q. Pham
*Attorney, Agent, or Firm*—James D. Welch

[57] ABSTRACT

The use of ellipsometry and polarimetry in analysis of partially polarized beams of electromagnetic radiation, such as result from simultaneous ellipsometric investigation of a plurality of identifiably separate laterally disposed regions on a patterned sample system, is disclosed. Practice of the present invention methodology enables evaluation of characterizing representative parameters of partially polarized beams of electromagnetic radiation, and laterally and vertically oriented physical dimensions and/or optical property (s) of at least two identifiably separate laterally disposed regions of a partially depolarizing sample system. The present invention identifies partially polarized electromagnetic beam characterizing partitioning representative parameter(s) which quantify electromagnetic beam intensity resulting from coherent and from incoherent addition of electric fields, respectively, as well as electromagnetic beam spacial and/or temporal coherence and degree of collimation characterizing representative parameters as mathematical model parameters which can be evaluated, in addition to investigated patterned sample system laterally and vertically oriented physical dimensions and/or optical property(s) characterizing representative parameters. The depolarizing effects of backside reflections associated with layers in sample system region(s) are also be included.

18 Claims, 7 Drawing Sheets

Beam entirely within the etched region:
| 1 | oxide final | 1.7837 nm |
|---|---|---|
| 0 | si final tabulated | 1 mm |
FIG. 7a
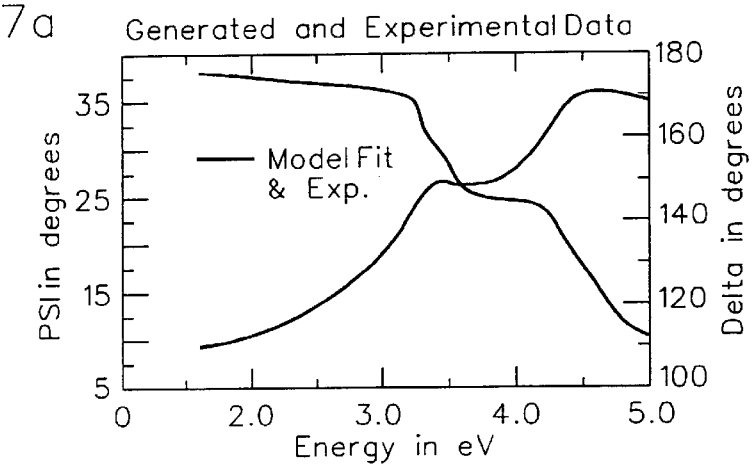
FIG. 7b
Beam entirely within the unetched region:
| 2 | oxide final | 98.627 nm |
|---|---|---|
| 1 | oxide final | 1.7837 nm |
| 0 | si final tabulated | 1 mm |
FIG. 8a
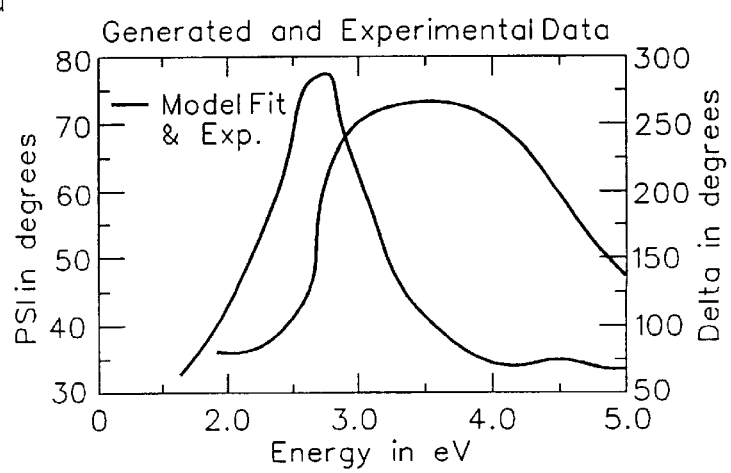
FIG. 8b Beam overlapping both etched and unetched regions:
| 2 | oxide final | 98.752 nm |
|---|---|---|
| 1 | oxide final | 1.8176 nm |
| 0 | si final tabulated | 1 mm |
FIG. 9a
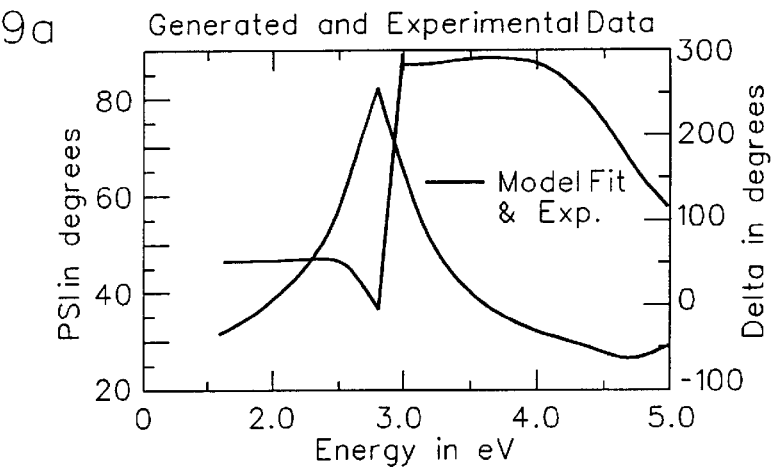
FIG. 9b
| MSE = 4.605 | |
|---|---|
| Thick.2 | 98.752±0.365 |
| Thick.1 | 1.8176±0.364 |
| ThkUni | 14.034±0.247 (% of unetched area in beam) |
FIG. 9c
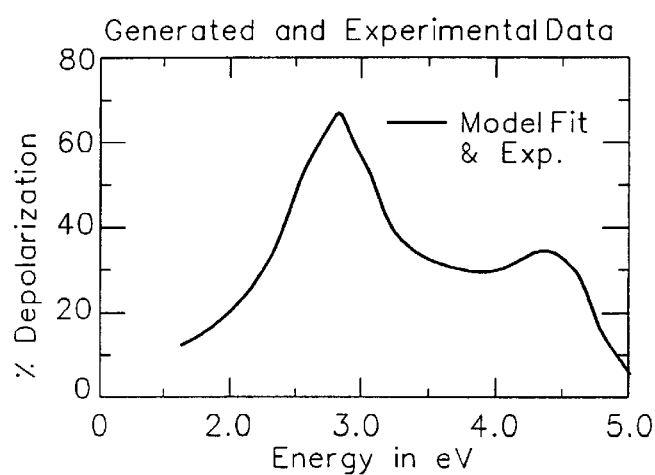
FIG. 9d

| 1 | Intermix | 2.6716 nm |
|---|---|---|
| 0 | Microscope slide glass | 1.5 nm |
| -1 | Intermix | 5.1258 nm |
FIG. 10a
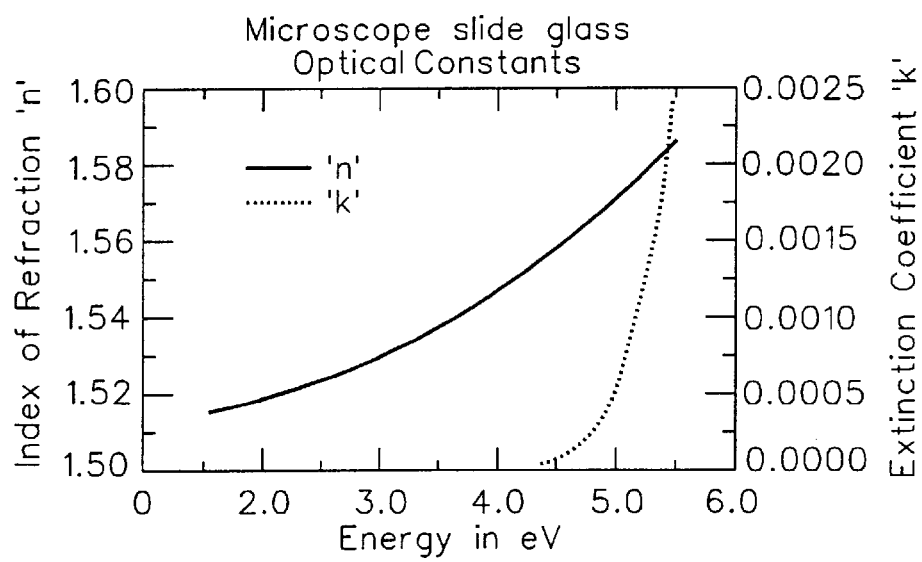
FIG. 10b
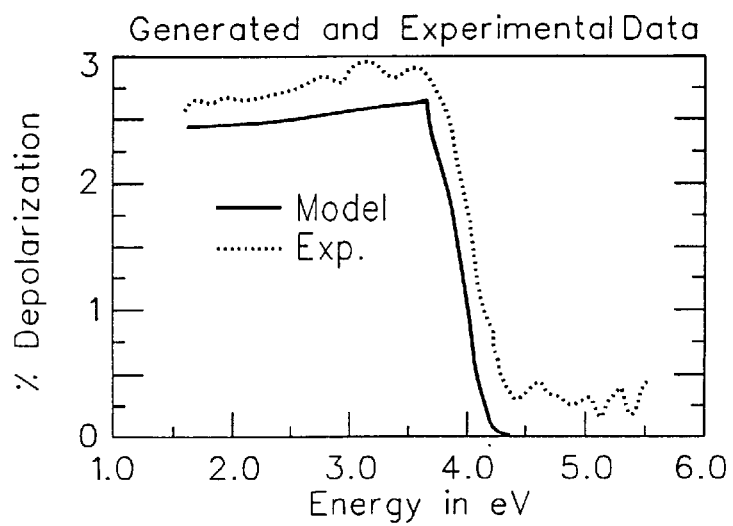
FIG. 10c

ANALYSIS OF PARTIALLY POLARIZED ELECTROMAGNETIC RADIATION IN ELLIPSOMETER AND POLARIMETER SYSTEMS

TECHNICAL FIELD

The present invention relates to ellipsometry and polarimetry generally, and more particularly to analysis of singly, partially and/or multiply polarized beams of electromagnetic radiation such as can result from simultaneous ellipsometric investigation of a plurality of identifiably separate laterally disposed regions on a patterned sample system, typically to the end that characterizing representative parameters of a partially polarized beam of electromagnetic radiation, and vertically oriented physical dimensions and/or optical property(s) of at least two identifiably separate laterally disposed regions, are simultaneously evaluated. The present invention can be practiced in-situ and ex-situ.

BACKGROUND

Polarized beams of electromagnetic radiation can be singly, partially, or multiply polarized and can be characterized by representative characteristic parameters such as:
degree(s) of temporal coherence,
degree(s) of spatial coherence,
wavelength bandwidth content,
degree(s) of collimation determining angular bandwidth, and intensity.

Continuing, in ellipsometer and polarimeter settings, expected experimentally obtained intensity values of polarized beams of electromagnetic radiation can be calculated using mathematical models which assume primarily "coherent", primarily "incoherent" and mixtures of "coherent" and "incoherent" addition of electric field components present therein. Coherent addition of electric fields to arrive at an Intensity is accomplished by:

$$I=(E1+E2+\ldots En)^*(E1+E2+\ldots +En)^*),$$

and incoherent addition of electric fields to arrive at an Intensity is accomplished by:

$$I=(E1^*E1^*)+(E2^*E2^*)+\ldots +(En^*En^*)).$$

(It is noted that each of the En's in the incoherent electric field addition Intensity equation can result from coherent addition of electric fields which result, for instance, from a multiplicity of electromagnetic waves which reflect from a single region on a patterned sample system).

To appreciate the present invention, it is to be understood that to date most work in ellipsometry has been focused upon investigation of relatively homogeneous regions in a sample system, and mathematical modeling of investigated sample systems and electromagnetic radiation utilized in investigation thereof, has proceeded with the assumption that coherent addition of electric fields accounts for experimentally measured intensities. That is, with a few exceptions, (see supra herein), the occurance of incoherent addition of electric fields in a beam of electromagentic radiation as a cause of intensity thereof has been largely unreported.

Incoherent addition of electric fields, and simultaneous coherent and incoherent electric field addition in electromagnetic radiation to produce a measurable intensity, however, can result where a polarized electromagnetic beam is caused to, for instance, interact with a sample system with identifiably separate laterally offset pattern regions present therein. This is the case as a portion of such a beam of electromagnetic radiation which travels one spatial pathway can have a definite phase relationship to portions of said beam of electromagnetic radiation which travels an alternative spatial pathway, thereby entering coherence related interference effects into production of an intensity signal and requiring that intensity be calculated by $(I=(E1+E2+\ldots En)^*(E1+E2+\ldots +En)^*)$, but it can also occur that portions of said beam of electromagnetic radiation which travel one spatial pathway have a lack of a distinct phase relationship to portions of said beam of electromagnetic radiation which travel an alternative spatial pathway, such that phase relationships between them are essentially negligible and require that intensity be calculated by $(I=(E1^*E1^*)+(E2^*E2^*)+\ldots +(En^*En^*))$, which describes incoherent addition of electric fields.

Continuing, ellipsometer, polarimeter and the like systems, allow determination of sample system physical, (such as thickness), and/or optical properties, (such as refractive index and extinction coefficient of one or more surface films therein or thereon). In particular, ellipsometer systems detect change in "Polarization State" of a beam of polarized light which is caused to interact with a Sample System, where Polarization State here refers to a set of values for Polarized Light Beam Orthogonal Components, (such as "S" and "P"), Magnitude Ratio, and a Phase Angle therebetween. (For general introductory background purposes, it is noted that "P" refers to that electric field component of a beam of electromagnetic radiation which is in a plane containing the normal to an investigated Sample System surface and an incident and/or transmitted beam of polarized light, and "S" refers to an electric field component of said beam of electromagnetic radiation which is perpendicular to said "P" component, and simultaneously parallel to the surface of said Sample System. It is also noted that a "full" polarization state also requires designation of an absolute value to which a magnitude ratio is referenced, and the direction of rotation of electric fields associated with a polarized beam of light).

Conventional use of ellipsometer systems provides the ability to analyze a sample system, and via appropriate transfer equations (specific to an ellipsometer system type), or other mathematical technique, (eg. regression), as applied to experimentally determined intensity data, return PSI and DELTA values which are representative of a "spot" on a Sample System, which "spot" presents with relatively constant vertically oriented thickness(es) and optical properties. Said PSI and DELTA are related as:

$$r_p/r_s = \text{Tan}(\psi)e^{i(\Delta)}$$

where $r_p$ and $r_s$ are the well known Fresnel Reflection Coefficients for P and S polarized electromagnetic radiation. (Note similar Transmission Fresnel Coefficients, $t_p$ and $t_s$, can be substituted to provide a similar equation for the case where a beam of electromagnetic radiation is caused to be transmitted through a Sample System. A book by Azzam and Bashara titled "Ellipsometry and Polarized Light", North-Holland, 1977 further describes Fresnel Coefficients, and is incorporated into this Disclosure by Reference).

Conventional teachings are then directed to use of ellipsometer systems to determine physical and/or optical properties of sample systems which are essentially homogeneous over a laterally dimensioned region "spot" of a sample system, upon which a beam of polarized electromagnetic radiation impinges, (that is the "spot" investigated on the sample system is essentially determined by an electromagentic beam spot size). Ellipsometry has not been widely applied in characterizing sample systems which contain patterns, (eg. sample systems which present with a plurality of identifiably separate laterally disposed regions present within a beam of polarized electromagnetic radiation "beam spot" size, at the location where a beam of electromagnetic radiation impinges upon a sample system). Of importance in the present invention, is the fact that where "patterned" samples are investigated by a beam of electromagnetic radiation, effects appear which do not appear in investigation of homogeneous sample systems. Said effects, in addition to mixed coherent and incoherent addition of electric fields, can also include shadowing, (where a beam of electromagnetic radiation caused to impinge thereupon and an angle to the surface thereof does not have access to certain regions on said patterned sample system adjacent to relatively vertically taller regions thereon).

A recent paper titled "Multiwavelength Ellipsometry for Real-Time Process Control of the Plasma Etching of Patterned Samples", by Maynard et al., J. Vac. Sci. Technol., B 15(1), Jan/Feb 1997, describes real-time determination of thickness of a film as it is etched. The technique involves analysis of ellipsometer detector provided intensity based upon an assumption of addition of coherent electromagnetic beam portions which simultaneously interact with different laterally disposed regions on a patterned sample system. The mathematical model reported in this paper, however, does not consider that electric fields in electromagnetic radiation which is caused to interact with a patterned sample system can combine incoherently to produce detector provided intensity instead of, or in addition to, coherent addition of electric fields, and assumes that the effects of diffraction are negligible.

A paper titled "In Situ Ellipsometry and Reflectometry During Etching Of Patterned Surfaces: Experiments And Simulations", by Haverlag and Oehrlien, J. Vac. Sci. Technol. B 10(6), Nov/Dec 1992, describes the effect of pattern orientation on a sample system investigated by ellipsometry. It is concluded that cases wherein a probe beam is directed parallel to, and cases wherein a probe beam is directed perpendicular to sample system line patterns must be modeled differently, but that etching procedure end point detection is possible. For the case where the probe beam is oriented parallel to sample system pattern lines, a sudden change in PSI-DELTA plane plots is observed at an etch procedure end point. Such a sudden change in PSI-DELTA plane plots is not observed at an etch procedure end point where the probe beam is oriented perpendicular to sample system pattern lines, however, and it is concluded that etch procedure end points in low vertical height to lateral dimension aspect ratio sample system patterning, in such a case, can be very difficult to detect. End point detection by the monitoring of a derivative of reflectivity is identified as an alternative technique.

A paper by Blayo et al, titled "Ultraviolet-Visible Ellipsometry For Process Control During The Etching Of Submicron Features", J. Opt. Soc. Am. A, Vol. 12, No. 3, March 1995 concludes that there exists an optimum spectral range that can be used for process control for etching patterned wafers. That is, said article identifies the importance of observing PSI and DELTA values at an appropriate wavelength in a spectroscopic range, (eg. 375.8 nm rather than 632.8 nm where etching of a specified multilayer stack was investigated), as sensitivity to the results of an etch process reported in this work do not appear in PSI and DELTA plots obtained at most wavelengths.

A paper tiled "In Situ And Ex Situ Applications Of Spectroscopic Ellipsometry", Mat. Research, Soc. Proc., Vol. 324, 1994, by Woollam et al., describes application of ellipsometry to investigation of single films, flat panel displays, and in situ semiconductor growth and deposition control. Tracking of variables such as PSI, DELTA and refractive indicies as functions of independent variables such as wavelength and sample system layer depth, is identified.

Another paper by Maynard and Hershkowitz, titled "Thin-Film Interferometry Of Patterned Films", J. Vac. Sci. Technol. B, Vol 13, May/June 1995, describes the use of interferometry to determine the thickness of thin films on patterned sample systems. The mathematical modeling and analysis techniques are applicable to sample system pattern features which are smaller than the wavelength of light utilized to investigate them. This is essentially equivalent to saying that coherent addition of electric fields, with any accompanying interference effects, is assumed.

A paper titled "Optical Etch-Rate Monitoring: Computer Simulation Of Reflectance", by Heimann et al., J. Electochem. Soc., Vol. 131, No. 4, April 1984, reports numerical simulation of a signal from a laser etch-rate monitor which utilizes changes in reflectance from a multilayer structure while the top layer is being etched. Another paper titled "Optical Etch-Rate Using Active Device Areas: Lateral Interference Effects", by Heimann, J. Electochem. Soc., Vol. 132, No. 8, August 1985, describes the analysis of Reflectance data to determine end point etching of polysilicon.

A paper titled "Spectral Ellipsometry On Patterned Wafers", by Duncan et al., SPIE, Vol. 2637, April 1995 describes application of a modulation element ellipsometer in investigation of a one-dimensional etched, rectangular groove geometry pattern on a semiconductor substrate. Zeroth-order reflection coefficients for orthogonal P and S polarization states are utilized as are models for ellipsometric PSI and DELTA. The effect of groove geometry on PSI and DELTA is investigated.

A paper titled "Optical Analysis Of Complex Multilayer Structures Using Multiple Data Types", by Johs et al., SPIE, Vol. 2253, 1994, describes the importance in considering back-side reflections in multiple layer sample systems. A paper by Jellison titled "Sample Depolarization Effects From Thin Films of ZnS on GaAs As Measured By Spectroscopic Ellipsometry", Appl. Phys. Lett. 61 (5) Aug. 1992 is also identifed as providing insight of results investigation of thin films with thickness gradients present therein. Another paper which is expected to be published in Thin Film Solids" in 1997, was presented by Jellison at the Second International Conference on Spectroscopic Ellipsometry in Charleston, N.C. Reported were the results of investigation of uneven depth film utilizing incoherent addition of electric fields, but not discussed was investigation of patterned sample systems wherein separately identifiable laterally disposed regions are present thereon, which sample system geometry, it is noted, can require mathematical modeling which assumes partially coherent and partially incoherent addition of electric fields in arriving at an electromagnetic beam intensity value which is measured at a detector for a singly, multiply or partially depolarized beam of electromagnetic radiation which is caused to interact with a patterned sample system and enter said detector.

Continuing, ellipsometer and polarimeter systems can be generally, broadly classified as:
1. Rotatable Element or Intensity Modulating Rotating Element Ellipsometers (REE); and
2. Phase Modulating Modulation Element Ellipsometers (MEE).

An example of a rotating analyzer ellipsometer (RAE) system, for instance, is presented in a Patent to Woollam et al., U.S. Pat. No. 5,373,359. Additional Patents to Johs et al. and Green et al., U.S. Pat. Nos. 5,504,582 and 5,521,706 respectively provide further insight into rotating analyzer ellipsometer (RAE) systems. Another U.S. Pat. No. 5,416,588 to Ducharme et al., describes a Modulation Element Ellipsometer (MEE). While the specifics of signal generation are different in (REE) and (MEE) ellipsometers, and even amongst Ellipsometers of similar type, the end result of utilization thereof is provision of PSI and DELTA values, (or similar related parameters such as Fourier Coefficients or Mueller Matrix related parameters "N" "IS" and "C" identified by Jellison for modulation element ellipsometer systems), for Sample Systems analyzed therein. This is the case regardless of Sample System type (eg. isotropic, anisotropic, or anisotropic and depolarizing).

Numerous other Ellipsometer Systems could be described, which are, for instance, comprised of various combinations of:
Stationary Polarizer(s);
Stationary Compensator(s);
Stationary Analyzer(s);
Rotatable Polarizer(s);
Rotatable Compensator(s);
Rotatable Analyzer(s);
Rotating Polarizer(s);
Rotating Compensator(s);
Rotating Analyzer(s); and
Modulator Element(s).

Examples of Ellipsometers which can practice the method of the present invention method are, for instance:
a. Rotatable Element Nulling Ellipsometers (RENE);
b. Rotatable Element Automated Nulling Ellipsometers (REANE);
c. Modulation Element Ellipsometers (MEE);
d. Rotating Analyzer Ellipsometers (RAE);
e. Rotating Polarizer Ellipsometers (RPE);
f. Rotating Compensator Ellipsometers (RCE);
g. Rotating Polarizer and Analyzer Ellipsometers (RPAE);
h. Rotating Polarizer and Analyzer, Fixed Compensator (RPAFCE);
i. Rotating Analyzer and Compensator, Fixed Polarizer Ellipsometer (RACFPE);
j. Rotating Polarizer and Compensator, Fixed Analyzer (RPCFAE);
k. Rotating Analyzer, Fixed Polarizer and Compensator Ellipsometer (RAFPCE);
l. Rotating Polarizer, Fixed Analyzer and Compensator Ellipsometer (RPFACE);
m. Rotating Compensator, Fixed Analyzer and Polarizer Ellipsometer (RCFAPE);
(Note that similar identifying descriptions also apply to Polarimeter and the like Systems and that for the purposes of the present invention it is not necessary to describe each above listed system in detail.)

Regardless of ellipsometer type, however, a common result is the production of an intensity signal by a detector system which is positioned to intercept an electromagnetic beam which has interacted with a sample system, which intensity signal is the result of all effects caused by ellipsometer system components and a sample system interacted with. As well, it is beneficial to consider that the effects of all components of a specific ellipsometer system can be eliminated from collected data, leaving only information present which pertains to an investigated sample system per se., (ie. only the effects of the interaction of a polarized beam of electromagnetic radiation with a sample system, on said polarized beam of electromagentic radiation, remain). This concept should be kept in mind regarding the present invention because, again for emphasis, the present invention can be practiced with essentially any ellipsometer/polarimeter system wherein a change of polarization state in a beam of singly, partially or multiply polarized electromagnetic radiation, which change results from the interaction thereof with a sample system, is analyzed to provide insight to optical and physical properties of said investigated sample system.

As alluded to, until recently, (eg. Maynard et al. and other papers), published results of the application of ellipsometry have focused upon the investigation of sample systems which are essentially non-depolarizing and where an electromagnetic beam spot caused to impinge upon a sample system falls entirely on a region of said sample system which does not contain patterned edges or regions. Ellipsometry has not been generally adapted to simultaneously investigate a plurality of identifiably separate laterally disposed regions (with respect to one another), on a patterned sample system.

A need for improved and expanded ellipsometry procedures which provide for electric fields to be modeled as being incoherently combined to allow calculation of experimentally determined detector provided intensity instead of, or in addition to, coherent addition of electric fields, has thus been identified. It is disclosed that the J. A. Woollam Co. WVASE, (Registered Trademark), computer program, with enabling adaptation, is applicable to facilitating practice of the present invention method.

DISCLOSURE OF THE INVENTION

The present invention comprises a general approach to the investigation of partially polarized electromagnetic beams which are characterized by some degree of temporal and/or a spatial coherence, a wavelength bandwidth content, and an angular bandwidth, (ie. degree of collimation), content. In addition, the present invention provides that intensity monitored by a detector system, (eg. such as in an ellipsometer/polarimeter system), be considered as having been produced by other than purely coherent addition of electric fields. In particular a beam "partition" parameter is included in mathematical modeling which designates a percentage of a beam of electromagnetic radiation which is comprised of electric field elements that add coherently. The remaining portion of said beam of electromagnetic radiation is considered to result from incoherent addition of electric fields. Of course, it is to be understood, said partition parameter can be zero (0.0) or one (1.0), indicating purely coherent or purely incoherent addition of electric fields, depending on how the partition parameter is defined.

At this point it is noted that polarized electromagnetic beam investigation of sample systems which have surface layer(s) present thereon, which layer(s) are not homogeneous but rather are the result of combined regions of different composition, (eg. polysilicon and voids), is often approached by use of an Effective Media Approximation, (EMA). Said (EMA) approximation effectively identifies said surface layer(s) as each being "X %" composed of one component intermixed with (100-"X"%) of another component. Said approach works for small component domain regions, (eg. of Angstrom dimensions), but as "domain regions" of surfaces of sample systems become relatively larger, (eg. patterned regions comprising identifiably separate laterally disposed regions with micron dimensions), the (EMA) approximation becomes inaccurate, and it becomes necessary to consider how a polarized electromagnetic beam is effected by interaction therewith, (ie. becomming partially depolarized), and how electric fields in said (partially depolarized), electromagnetic beam present after interaction with a patterned sample system, add, (eg. coherently and/or incoherently), to determine an Intensity signal, measurement of which typically mediates analysis of such a patterned sample system. The (EMA) approximation generally assumes no electromagentic beam depolarization occurs. The Effective Media Approximation (EMA) is better described in "Handbook Of Optical Constants Of Solids", published by Academic Press, 1985, edited by Palik, in a section thereof authored by D. E. Aspnes; said reference being incorporated by reference hereinto.

It is also noted that films of laterally uneven thickness can serve to affect a beam of polarized electromagnetic radiation caused to interact therewith, such that said beam becomes depolarized and such that assumption of incoherent addition of electric fields becomes necessary to calculate intensity monitored at a detector thereof. However, in the case of uneven film thickness, it is generally considered that said film composition is essentially laterally homogeneous and that optical constants in one region are essentially similar to those in laterally disposed regions. The present invention, on the other hand, assumes that various, (at least two), identifiably separate laterally disposed regions have very different effective optical constants, in addition to possibly different thicknesses. For instance, an etched region on a sample system is comprised of essentially ambient atmosphere, while an adjacent unetched region has regional sample system composition. (Note that this does not mean that an identifiably separate laterally disposed region on a patterned sample system can not have effective optical constants and a thickness essentially equivalent to effective optical constants and a thickness in another identifiably separate laterally disposed region, or that a plurality of identifiably separate laterally disposed region can not have essentially the same effective optical constants and thickness, (all etched regions for instance). It means only that at least two regions on a patterned sample system present with different, one to the other, optical constants and/or thickness).

In a preferred embodiment, the present invention then assumes the presence of a partially depolarizing patterned sample system which is to be investigated, which partially depolarizing patterned sample system comprises a plurality of identifiably separate laterally disposed, (ie. laterally offset from one another) regions, said identifiably separate laterally disposed regions each being comprised of various vertically oriented layers and/or compositions and presenting with various effective optical constants and thicknesses. For instance, one such region might comprise a vertically oriented sequence of silicon substrate, a first depth of silicon dioxide, aluminum and perhaps photo-resist, while a laterally adjacent region might comprise only the silicon substrate, (eg. after an etch procedure). Another identifiably separate laterally positioned region might comprise silicon substrate, a second depth of silicon dioxide, and polycrystalline silicon. Again, each identifiably separate laterally offset (from one another) region has effective optical constants and a thickness associated therewith. Said identifiably separate laterally offset (from one another) regions can be of dimensions varying from sub-micron to hundreds of microns or larger in various directions. For instance a MOSFET Gate might be of a sub-micron width, but many microns long. In addition, various regions can be of step or gradual geometric shape, can comprise vertically graded layers, can be isotropic or anisotropic, and can be depolarizing or non-depolarizing. There are essentially no limitations placed on sample system structure.

In a typical embodiment, the present invention assumes the presence of an ellipsometer system, which can be of any type, (eg. rotating element or modulation element ellipsometer, such as briefly described in the Background Section of this Disclosure). Said ellipsometer system is present to provide a singly, partially, or multiply polarized beam of electromagnetic radiation of some degree of temporal and/or a spatial coherence, of a wavelength bandwidth content, and of an angular bandwidth (ie. degree of collimation) content. Said beam of electromagnetic radiation is caused to impinge upon said patterned sample system, in use, at desired angle(s) of incidence, such that a desired electromagnetic beam spot size is achieved on said patterned sample system and an intended electromagnetic beam spot size area is effected, which area contains a number of sample system laterally offset regions therewithin where said electromagnetic beam impinges upon said patterned sample system. In some cases the sample system can also be caused to assume different orientations, such as by rotation. In fact a sample system can be caused to constantly rotate during data acquisition, thereby providing periodic Intensity information regarding sample system patterning "aspect ratio" geometry as "viewed" from positions corresponding to a circumscribing three-hundred-sixty (360) degrees. This can provide information not available from one viewpoint because of the effects of, for instance, "shadowing", (where relatively large vertical and relatively small lateral dimensions of separately identifiable laterally disposed regions on a sample system surface prevent an electromagnetic beam, caused to impinge thereupon at an angle to said sample system surface, from interacting with various portions of various of said separately identifiable laterally disposed regions).

In use said beam of electromagnetic radiation is caused to interact with said patterned sample system and a detector system in said ellipsometer system is caused to intercept a resulting reflected and/or transmitted specular zeroth-order.

The present invention then generally provides that an intensity of an electromagnetic beam be modeled as resulting partially from coherent addition of electric fields, and partially from incoherent addition of electric fields, however, cases can develop where essentially purely coherent addition, or more relevantly, essentially purely incoherent addition of electromagnetic fields occur. That is to say, where a plurality of separately identifiable laterally disposed regions are within a spot size of, and simultaneously investigated by, a single beam of singly, partially or multiply polarized electromagnetic radiation which impinges upon a sample system, it is often the case that assumption of purely incoherent addition of electric fields is appropriate. Demonstrative results of this are discussed in the Detailed Description Section of this Disclosure in conjunction with PSI and DELTA and Percent Depolarization Polts which are presented in the Drawings.

The present invention can also include accounting for the effects of back-side reflections, where, for instance, an impinging electromagnetic beam partially reflects from a top-most surface, and a portion thereof reflects from a lower surface, (eg. a transparent glass substrate of one (1.0) or so millimeter deep). Note that back-side reflections can be an important cause of partial depolarization of an essentially polarized beam of electromagnetic radiation, leading to incoherent electric field addition effects being present.

The present invention then requires that intensity data provided by a detector system in an ellipsometer system be analyzed with proper assumptions made regarding coherence of electric fields which result from electromagnetic beam portions which interact with each identifiably separate laterally disposed pattern region on a sample system. If resulting electric fields in electromagnetic beam partitioned parts are "coherent", (eg. portions of said electromagnetic beam which travel one spatial pathway have a definite phase relationship to portions of said electromagnetic beam which travel an alternative spatial pathway, thereby potentially entering interference effects into production of an intensity signal), then phase relationships between them must be considered in arriving at intensity, whereas if electric fields in electromagnetic beam partitioned parts are "incoherent", then said phase relationships are essentially negligible. One then must perform electromagnetic beam intensity analysis while assuming summation of electric fields, (where coherent phase angle effects are relevant), produced said intensity, or by summation of intensities, (where coherent phase angle effects are irrelevant). That is, a measured electromagnetic beam intensity must be considered as resulting from:

Coherent $(E1+E2+\ldots+En)^*(E1+E2+\ldots+En)^*$; or

Incoherent $(E1^*E1)+(E2^*E2^*)+\ldots+(En^*En^*)$;

(where En*, for instance, indicates conjugation of electric field component En),
addition, or perhaps some combination thereof.

It is noted that various "portions" of an electromagnetic beam caused to impinge upon a patterned sample system interact with different identifiably separate laterally offset, (from one another), pattern regions thereon, however, said electromagnetic beam can also be considered to be "partitioned" into first and second parts where said first and second "partitioned parts" represent fractions of said electromagnetic beam which effect intensity thereof by coherent, and by incoherent addition of electric fields, respectively. As utilized herein, it is to be well understood that electromagnetic beam "portions" and electromagnetic beam "partitioned parts" are very different. As an example, fifty (50%) percent of the cross sectional area of an electromagnetic beam might fall in one portion, (ie. identifiably separate laterally oriented pattern region on a sample system), while fifty (50%) percent thereof falls upon a second identifiably separate laterally oriented pattern region. However, it can occur that, for the same sample system, coherent electric field addition occurs in only a "partitioned" ten (10%) percent of said electromagnetic beam as a result. It is very important to keep said described distinction between electromagnetic beam "portions" and "partitioned parts" in mind, when electromagnetic beam modeling partition characterizing representative parameter(s) are referred to herein.

The difference between electromagnetic beam "portions" and "partitioned parts" can perhaps be better appreciated by reference to the mathematical expressions for Sample System representing PSI and DELTA, (for Rotating Analyzer and Rotating Polarizer Ellipsometers). In the following expressions it is to be understood that while electromagnetic beam "portions" interact with various regions of a sample system, (as assigned via weighting factors), it is possible that total coherent, or total incoherent addition can occur. That is the electromagnetic beam "partitioning" can be effectively zero (0.0) or one-hundred (100) percent, depending on how it is considered.

FOR COHERENT CASE:

$$R'_P = \sum_i w_i R_P$$

$$R'_S = \sum_i w_i R_S$$

$$\text{Tan}(\psi') = \left|\frac{R'_P}{R'_S}\right|$$

$$\text{Tan}(\Delta') = \arg\left(\frac{R'_P}{R'_S}\right)$$

FOR INCOHERENT CASE:

$$\text{Tan}(\psi_{\mathit{eff}}) = \sqrt{\frac{\sum_i w_i(R_{P_i} \cdot R^*_{P_i})}{\sum_i w_i(R_{S_i} \cdot R^*_{S_i})}}$$

$$\text{Cos}(\Delta_{\mathit{eff}}) = \frac{\sum_i w_i \text{Re}(R_{P_i} \cdot R^*_{S_i})}{\sqrt{\sum_i w_i(R_{P_i} \cdot R^*_{P_i}) \cdot \sum_i w_i(R_{S_i} \cdot R^*_{S_i})}}$$

where $(w_i)$ identifies a weighting factor which identifies how much of an electromagnetic beam Interacts with an identifiably distinct laterally disposed region, (eg. "portion") of a patterned sample system.

Continuing, where it is the case that both coherent and incoherent effects are present, an effective "partitioning factor" of other than zero (0.0) or one-hundred (100) percent would be present to determine the relative effects of said coherent and incoherent electric field addition. It should be readily apparent that said "partitioning factor" would control the relative effects of coherent addition and incoherent addition which lead to PSI and DELTA values, and that is quite distinct from said weighting factor $(w_i)$. That is, the "partitioned part" of a beam of electromagnetic radiation which is governed by coherent addition of electric fields and the "partitioned part" thereof which is governed by incoherent addition of electric fields is quite distinct from the amount of said beam of electromagnetic radiation which physically interacts with a portion of a sample system.

It should be noted that the above equations provide only TAN($\psi$) and COS($\Delta$). For ellipsometer systems containing a retarder it is possible to obtain TAN($\psi$), COS($\Delta$) and SIN ($\Delta$). The presence of a retarder allows one to determine the "handedness" of a beam of electromagnetic radiation and that identifies if an angle is between zero (0.0) and one-hundred-eighty (180) degrees or is between one-hundred-eighty (180) degrees and three-hundred-sixty (360) degrees. (The SIN Function is of opposite sign in said two angle ranges and the presence of the retarder allows determination of said sign). Where a retarder is present, calculation of a Percent Depolarization factor can be performed as follows:

$$\text{Tan}(2\psi_{\text{eff}}) = \frac{\sqrt{\left(\sum_i w_i \text{Re}(R_{P_i} \cdot R_{P_i}^*)\right)^2 + \left(\sum_i w_i \text{Im}(R_{P_i} \cdot R_{P_i}^*)\right)^2}}{\sum_i w_i (R_{P_i} \cdot R_{P_i}^*) \cdot \sum_i w_i (R_{S_i} \cdot R_{S_i}^*)}$$

$$\text{Tan}(\Delta_{\text{eff}}) = \frac{-\sum_i w_i \text{Im}(R_{P_i} \cdot R_{S_i}^*)}{\sum_i w_i \text{Re}(R_{P_i} \cdot R_{S_i}^*)}$$

$$\% \text{Dep} = 100\left\{1 - \frac{\left(\sum_i w_i R_{P_i} \cdot R_{P_i}^* - \sum_i w_i R_{S_i} \cdot R_{S_i}^*\right)^2 + 4\left(\left(\sum_i w_i \text{Re}(R_{P_i} \cdot R_{P_i}^*)\right)^2 + \left(\sum_i w_i \text{Im}(R_{P_i} \cdot R_{P_i}^*)\right)^2\right)}{\left(\sum_i w_i R_{P_i} \cdot R_{P_i}^* - \sum_i w_i R_{S_i} \cdot R_{S_i}^*\right)^2}\right\}$$

It is noted then that data provided by any ellipsometer system in which a retarder element is caused to be present between a source of an electromagnetic beam and a detector system, can be manipulated to remove the effects of ellipsometer system components, including said retarder element, with a resulting data set being definitive of optical and physical properties of an investigated sample system per se. Said resulting data set can then be analyzed assuming intensity measured at an ellipsometer system detector was the result of addition of electric fields on an at least partially incoherent basis, (eg. addition of intensities).

At this point it is also noted that electromagnetic beam wavelength bandwidth and angular bandwidth, (ie. degree of beam collimation), can also be accounted for by inclusion of terms in said summations, with appropriate weighting factors assigned to each term. For instance, for each separately identifiable laterally disposed region included in the summation, a multiplicity of wavelength and/or angular bandwidth terms can be included. It will be appreciated that while the number of terms in the summations increase dramatically, the computations which account for said electromagnetic beam deviations from ideality are not essentially different for a multiplicity of wavelength and/or a multiplicity angular bandwidth terms, when compared to the calculations required to account for the presence of a multiplicity of separately identifiable laterally disposed regions in a sample system.

Continuing, the present invention, in its preferred embodiment, requires that one propose a model for all identifiably separate laterally disposed regions on an investigated patterned sample system, which fall within an investigating electromagnetic beam "spot size", at the point where it is incident upon said patterned sample system. That is, each separately identifiably laterally disposed region should be postulated as consisting of some sequence of vertically oriented of layers, each layer having associated therewith a thickness and optical constants. Said preferred present invention embodiment then requires that, for instance, a simultaneous regression of all model parameters selected as variable be performed onto experimentally obtained data, to determine if the proposed model, (with, for instance, least square error reducing adjustments to initially proposed and evaluated "fit parameter" variables introduced), can account for the experimentally obtained intensity data, in view of an appropriate coherent/incoherent electric field addition "partition parameter", which can also be a mathematical model "fit parameter". (It is noted that parameter evaluation approaches other than regression can also be utilized, such as neural network techniques).

In a basic form, the present invention can then comprise a method of analyzing a partially polarized electromagnetic beam, regardless of its source, comprising the providing of a partially polarized electromagnetic beam and the measuring of intensity data therefore; followed by providing a mathematical model for said partially polarized electromagnetic beam under the assumption that said intensity data results from simultaneous partially coherent:

$$[(E1+E2+\ldots+En)*(E1+E2+\ldots+En)^*]$$

and partially incoherent:

$$[(E1^*E1^*)+(E2^*E2^*)+\ldots+(En^*En^*)]$$

addition of electric fields in partitioned areas thereof, respectively. Distinguishing over typical conventional Polarimeter Systems methodology, the present invention mathematical model includes at least one partially polarized electromagnetic beam characterizing representative parameter selected from the group consisting of: (a wavelength bandwidth content characterizing representative parameter, and of degree of collimation determining angular bandwidth characterizing representative parameter).

In addition, said mathematical model can contain at least one degree of temporal and/or spatial coherence characterizing representative parameter(s), and at least one partially polarized electromagnetic beam partition characterizing representative parameter(s) which identifies what percentage of said partially polarized electromagnetic beam intensity results from partially coherent:

$$[(E1+E2+\ldots+En)*(E1+E2+\ldots+En)^*]$$

and what percentage results from partially incoherent:

$$[(E1^*E1^*)+(E2^*E2^*)+\ldots+(En^*En)]$$

addition of electric fields. Said method continues with evaluation of at least one partially polarized electromagnetic beam characterizing representative parameter(s) of said mathematical model using said measured intensity data, by a method selected from the group consisting of ("square error reducing mathematical regression", and "other than square error reducing mathematical regression").

As alluded to infra herein, it is to be understood that cases can occur where an electromagnetic beam is essentially fully the result of coherent, or essentially fully the result of incoherent, addition of electric fields. The present invention includes such cases, particularly where electromagnetic beam characterizing representative parameter(s) selected from the group consisting of: (a wavelength bandwidth content characterizing representative parameter, and of degree of collimation determining angular bandwidth characterizing representative parameter), is/are present in a mathematical model therefore.

A modified method of analyzing a partially polarized electromagnetic beam can comprise the steps of providing a sample system to an ellipsometer system, where said ellipsometer system comprises a polarization state generator, means for presenting a sample system, and a polarization state detector. Said method then comprises the steps of experimentally obtaining ellipsometric data from said polarization state detector; proposing an ellipsometer system and sample system representative parameter containing mathematical model; and evaluating representative parameter(s) of said ellipsometer system and sample system mathematical model with an assumption that experimentally obtained data provided by said polarization state detector results from simultaneous partially coherent and partially incoherent effects in production of said experimentally obtained ellipsometric data. Said method of analyzing a partially polarized electromagnetic beam can involve experimentally obtaining intensity data from a partially polarized electromagnetic beam which is obtained by causing said polarization state generator to provide a polarized beam of electromagnetic radiation; causing said polarized beam of electromagnetic radiation to interact with said sample system, which is a partially depolarizing sample; and causing a resulting assumed partially polarized beam of electromagnetic radiation to enter said polarization state detector whereby a representative intensity signal is developed said representative intensity signal being the result of simultaneous partially coherent:

$$[(E1+E2+\ldots+En)^*(E1+E2+\ldots+En)^*]$$

and partially incoherent:

$$[(E1^*E1^*)+(E2^*E2^*)+\ldots+(En^*En^*)]$$

addition of electric fields in forming said assumed partially polarized beam of electromagnetic radiation. (It is again noted that an intermediate step can be an elimination of the effects of ellipsometer system components on said experimentally obtained representative intensity signal, leaving an intensity signal which is the result of, only, interaction of a beam of electromagnetic radiation with a sample system. Where this is done an appropriate mathematical model then contains only characteristic parameters of an investigated patterned sample system).

A modified method of investigating a partially polarized electromagnetic beam comprises selecting representative parameters of an electromagnetic beam from the group consisting of (a degree of temporal coherence, a degree of spatial coherence, a wavelength bandwidth content, and of degree of collimation determining angular bandwidth). This is followed by causing a polarized electromagnetic beam to interact with a sample system comprising a plurality of laterally disposed regions, with a resulting specular zeroth-order of said polarized electromagnetic beam which results from said interaction, being caused to enter a detector system such that intensity data is experimentally obtained.

Next a mathematical model for the specular zeroth-order electromagnetic beam and sample system is proposed, in which said mathematical model said specular zeroth-order electromagnetic beam is considered as partitioned into first and second parts, and such that said obtained intensity data is considered to be the result of simultaneous partially coherent:

$$[(E1+E2+\ldots+En)^*(E1+E2+\ldots+En)^*]$$

and partially incoherent:

$$[(E1^*E1^*)+(E2^*E2^*)+\ldots+(En^*En^*)]$$

addition of electric fields, respectively, in said first and second partitioned parts of said specular zeroth-order electromagnetic beam. Said mathematical model further comprises characterizing parameters representative of at least some of said plurality of laterally disposed regions and in practice selected representative parameter(s) which characterize said specular zeroth-order electromagnetic beam and at least two of said plurality of laterally disposed regions in said mathematical model of said sample system are evaluated, utilizing said experimentally obtained intensity data. The method can further include, in the step of proposing a mathematical model for the specular zeroth-order electromagnetic beam and sample system, accounting for at least one selection from the group consisting of (effects of lateral and vertical dimensions of at least one of said plurality of laterally disposed regions, and effects of backside reflections caused by interfacing between vertically nonhomogeneous layers in at least one of said plurality of laterally disposed regions).

Another modified method of sample system investigation involving a partially polarized beam of electromagnetic radiation, involves providing an ellipsometer system comprising means for causing a singly, partially or multiply polarized beam of electromagnetic radiation selected from the group consisting of (singly, partially and multiply polarized), to interact with a sample system and enter means for detecting a resulting beam of electromagnetic radiation after said interaction with said sample system. This is followed by placing a sample system, which comprises a plurality of laterally disposed regions, into said ellipsometer system. Next the step of causing a singly, partially, or multiply polarized beam of electromagnetic radiation to interact with said sample system such that a resulting specular zeroth-order thereof, which results from said interaction, is caused to enter said means for detecting said polarized beam, is performed, such that specular zeroth-order electromagnetic beam and sample system characterizing ellipsometer intensity data is experimentally obtained. This is followed by proposing a mathematical model for the specular zeroth-order beam of electromagnetic radiation and sample system, in which mathematical model said specular zeroth-order beam of electromagnetic radiation, present after interaction of said polarized electromagnetic beam with said sample system, is considered as partitioned into first and second parts, and such that said obtained ellipsometric intensity data is assumed to be the result of coherent:

$$[(E1+E2+\ldots+En)^*(E1+E2+\ldots+En)^*]$$

and incoherent:

$$[(E1^*E1^*)+(E2^*E2^*)+\ldots+(En^*En^*)]$$

addition of electric fields, respectively, in said first and second partitioned parts of said specular zeroth-order electromagnetic beam present after interaction of said polarized electromagnetic beam of radiation with said plurality of laterally disposed regions in said sample system, which mathematical model further comprises characterizing parameters representative of at least some of said plurality of laterally disposed regions. Then evaluation of characterizing parameter(s) representative of at least one of said plurality of laterally disposed regions in said mathematical model of said sample system, utilizing said experimentally obtained intensity data, can be performed.

Said method can further comprise the step of identifying the relative relationship of wavelength to laterally disposed region dimensions and allocating a greater portion of said specular zeroth-order beam of electromagnetic radiation to said first partitioned part thereof, which involves coherent electric field addition, as the wavelength(s) present, relative to said laterally disposed regions dimensions therein become longer. As the wavelength(s) present, relative to said laterally disposed regions dimensions therein become shorter, allocation of a greater portion, (by manual setting or by mathematical model characteristic parameter fitting), of said specular zeroth-order beam of electromagnetic radiation to said second partitioned part of said specular zeroth-order beam of electromagnetic radiation, which involves incoherent electric field addition, is appropriate. Said method can further include the step of controlling the wavelength content of the polarized electromagnetic beam.

A present invention generalized method of simultaneously investigating a plurality of regions in a patterned sample system utilizing ellipsometry comprises the steps of providing a sample system which comprises a plurality of identifiably separate laterally offset regions, each of said identifiably separate laterally offset regions being comprised of vertically oriented layer(s) and/or composition(s). Said identifiably separate laterally offset regions each are typically of length and width dimensions varying from sub-micron and below to hundreds of microns and larger in various directions and each of said identifiably separate laterally offset regions contains at least one layer which is of a side elevational geometrical shape selected from the group consisting of (step or gradual), and of a vertically directed composition selected from the group consisting of (homogeneous and graded), each said identifiably separate laterally offset region having properties selected from the group consisting of (isotropic and anisotropic and depolarizing and non-depolarizing). Said method then continues with the providing of an ellipsometer system capable of producing a beam of electromagnetic radiation with a polarization state selected from the group consisting of (singly, partially and multiply polarized), said beam of electromagnetic radiation being characterized by degree(s) of temporal coherence, degree(s) of spatial coherence, wavelength bandwidth content, and a degree of collimation determining angular bandwidth. This is followed by causing a beam of electromagnetic radiation, as described, to impinge upon said patterned sample system at at least one desired angle(s) of incidence, such that for each angle of incidence a desired electromagnetic beam spot size is achieved on said patterned sample system and such that an intended number of identifiably separate laterally offset regions are included therewithin where said beam of electromagnetic radiation impinges upon said patterned sample system. A specular zeroth-order beam of electromagnetic radiation formed after interaction with said patterned sample system then is caused to enter a detector system in said ellipsometer system. Said method then involves providing a mathematical model of said ellipsometer system in combination with said patterned sample system, said mathematical model including representative characterizing parameters selected from the group consisting of (length and width, thickness(es) and optical constants for vertical layer(s) in identifiably separate laterally offset regions of said patterned sample system being simultaneously investigated, and for said beam of electromagnetic: radiation degree(s) of temporal coherence and degree(s) of spatial coherence, and a wavelength bandwidth content, and a degree of collimation determining angular bandwidth, and partition characterizing representative parameters which identify the percentage of said beam of electromagnetic radiation which effects an intensity value therefore by coherent addition of electric fields and the percentage thereof which effects an intensity value therefore by incoherent addition of electric fields, and for effects of layer interface and back-side reflections in identifiably separate laterally offset region). This is followed by performing a simultaneous regression of all selected model representative characterizing parameters onto experimentally obtained detector provided intensity data to determine if the proposed model, (with least square error reducing adjustments to initially proposed variables introduced), accounts for the experimental data in all simultaneously investigated identifiably separate laterally offset regions.

As mentioned with respect to previous recitation, said generalized method of simultaneously investigating a plurality of regions in a patterned sample system utilizing ellipsometry can further comprise selecting an approach to analysis of intensity data provided by said detector system in the ellipsometer system from the group consisting of:

(assuming primarily "coherence" of signals which result from parts of said beam of electromagnetic radiation which interact with identifiably separate laterally offset pattern regions, in that said part of said beam of electromagnetic radiation which travels one spatial pathway has a phase relationship to parts of said beam of electromagnetic radiation which travels an alternative spatial pathway, thereby possibly entering interference effects into production of an intensity signal and requiring that intensity be calculated by:

$$(I=(E1+E2+ \ldots +En)^*(E1+E2+ \ldots +En)^*);$$

and
assuming primarily "incoherence" of signals which result from parts of said beam of electromagnetic radiation which interact with identifiably separate laterally offset pattern regions, in that parts of said beam of electromagnetic radiation which travel one spatial pathway have a lack of phase relationship to parts of said beam of electromagnetic radiation which travel an alternative spatial pathway, such that phase relationships between them are essentially negligible and require that intensity be calculated by:

$$(I=[(E1^*E1^*)+(E2^*E2^*)+ \ldots +(En^*En^*)];$$

and
assuming a combination of "coherence" and "incoherence" effects thereby requiring simultaneous consideration of both intensity determining calculations:

$$(I=(E1+E2+ \ldots +En)^*(E1+E2+ \ldots +En)^*), \text{ and}$$

$$(I=[(E1^*E1^*)+(E2^*E2^*)+ \ldots +(En^*En^*)])).$$

Another method of sample system investigation, involving a partially polarized beam of electromagnetic radiation, can comprise providing an ellipsometer system which comprises means for causing a polarized beam of electromagnetic radiation, selected from the group consisting of (singly, partially and multiply polarized), to interact with a sample system and enter means for detecting a resulting beam of electromagnetic radiation after said interaction with said sample system. In this case said ellipsometer system is constructed to include means for controlling the wavelength content, and spot size of the polarized electromagnetic beam where it is caused to impinge upon and interact with said sample system, so as to control the number of laterally disposed regions present on said sample system which are therewithin. Next said method provides that a sample system, which comprises a plurality of laterally disposed regions be placed into said ellipsometer system, and that at at least one of a possible plurality of electromagnetic beam settings of at least one member of the group consisting of polarized electromagnetic beam (wavelength content and beam spot size), polarized beams of electromagnetic radiation be caused to interact with said sample system. A resulting specular zeroth-order thereof is caused to enter said means for detecting said polarized beam, such that specular zeroth-order electromagnetic beam and sample system characterizing ellipsometer intensity data is experimentally obtained. Next the step of proposing a mathematical model for the specular zeroth-order beam of electromagnetic radiation and sample system is performed. It is noted that in said mathematical model, said specular zeroth-order beam of electromagnetic radiation present after interaction of said polarized electromagnetic beam with said sample system, is considered as partitioned into first and second parts, such that said obtained ellipsometric intensity data is assumed to be the result of coherent:

$$[(E1+E2+\ldots+En)^*(E1+E2+\ldots+En)^*]$$

and incoherent:

$$[(E1^*E1^*)+(E2^*E2^*)+\ldots+(En^*En^*)]$$

addition of electric fields, respectively, in said first and second partitioned parts of said specular zeroth-order electromagnetic beam present after interaction of said polarized electromagnetic beam of radiation with said plurality of laterally disposed regions in said sample system. The mathematical model further comprises characterizing parameters representative of at least some of said plurality of laterally disposed regions. Finally, said method involves evaluating characterizing parameter(s) representative of at least one of said plurality of laterally disposed regions in said mathematical model of said sample system, utilizing said experimentally obtained intensity data.

Said method of sample system investigation can include, in the step of providing an ellipsometer system, providing an ellipsometer system with the capability of causing a sample system placed thereinto to assume various orientations, including continuous rotation of said sample system. Said method can also include the step of causing polarized beams of electromagnetic radiation to interact with said sample at a plurality electromagnetic beam settings of at least one member of the group consisting of polarized electromagnetic beam: (wavelength content and beam spot size), and can further include causing said sample system to assume a plurality of orientations; such that a resulting specular zeroth-order thereof, which results from said interaction, is caused to enter said means for detecting said polarized beam, such that specular zeroth-order electromagnetic beam and sample system characterizing ellipsometer intensity data is experimentally obtained for at least two sample system orientations.

Said method of sample system investigation can, in the step of placing a sample system which comprises a plurality of laterally disposed regions into said ellipsometer system, involve selecting a sample system from the group consisting of (a sample system with a plurality of essentially similar lateral dimension size laterally disposed regions; and a sample system with a plurality of laterally disposed regions of different lateral dimension sizes), and/or selecting a sample system with laterally disposed regions selected from a group consisting of (a sample system with similar vertically directed dimensions and/or compositions; and a sample system with different vertically directed dimensions and/or compositions).

Any method of the present invention involving investigating sample systems in ellipsometer systems can further comprise the step of controlling the spot size of the polarized electromagnetic beam where it is caused to impinge upon and interact with said sample system, so as to control the number of laterally disposed regions present on said sample system which are therewithin. (Note that spot size can be controlled by adjustment of the size of a present aperture through which said polarized electromagnetic beam is caused to pass in use).

Any method of the present invention involving investigating sample systems in ellipsometer systems can include evaluation of electromagnetic beam characterizing representative parameters selected from the group consisting of (a degree of temporal coherence, a degree of spatial coherence, a wavelength bandwidth content, and of degree of collimation determining angular bandwidth.)

Any method of the present invention involving investigating sample systems in ellipsometer systems can include evaluation of sample system characterizing representative parameters selected from the group consisting of (length and width dimensions, sample system feature size, thickness, and optical constants for vertical layer(s)), in identifiably separate laterally disposed regions of said sample system being simultaneously investigated.

It is further to be understood that steps and discussion presented in one method supra herein, can be deleted therefrom and/or substituted into other methods presented herein, and remain within the scope of the present invention. That is, the various methods recited are exemplary and not limiting.

It is noted that the J. A. Woollam Co. WVASE program presently allows regression onto up to ten, (ie. offset with respect to one another), types of regions in a patterned sample system, each of which regions is modeled as a vertical sequence of layers and/or compositions. (Note, it is possible to have many (eg. ten), identifiably separate laterally disposed regions present, but only a few different "types" of regions. That is, out of ten separately identifiable laterally disposed regions there may be three which are of essentially identical geometry and composition, but for lateral positioning, and five which are of another essentially identical geometry and composition, but for lateral positioning, with the remaining two being of distinct geometry and composition. In such a case, the present invention will detect effects of four different types of regions).

The present invention can be practiced in in-situ and ex-situ settings.

The present invention will be better understood by reference to the Detailed Description Section of the present Disclosure, in conjunction with the Drawings.

SUMMARY OF THE INVENTION

It is therefore a purpose of the present invention to describe the causing of an electromagnetic beam to interact with said patterned sample system and a detector system in an ellipsometer system such that said detector is caused to intercept a resulting reflected and/or transmitted specular zeroth-order, and that the intensity of said electromagnetic beam is, and should be modeled as resulting partially from coherent addition:

$$(E1+E2+\ldots+En)^*(E1+E2+\ldots+En)^*;$$

of electric fields, and partially from incoherent addition:

$$(E1^*E1^*)+(E2^*E2^*)+\ldots+(En^*En^*)$$

of electric fields.

It is another purpose of the present invention to teach that an electromagnetic beam "partitioning parameter" should be included in a mathematical model of an electromagnetic beam which defines what percentage of an intensity thereof is the result of coherent addition of electric fields and what percentage of an intensity thereof is the result of incoherent addition of electric fields.

It is yet another purpose of the present invention to teach a generalized approach to investigation and characterization of partially polarized electromagnetic beams which are characterized by some degree of temporal and/or a spacial coherence, a wavelength bandwidth content, and an angular bandwidth (ie. degree of collimation) content.

It is another purpose of the present invention to identify a source of partially polarized electromagnetic beam involves interaction between a singly, partially or multiply polarized beam of electromagnetic radiation and a partially depolarizing sample system comprising a plurality of identifiably separate laterally disposed, (ie. offset from one another) regions, said identifiably separate laterally disposed regions being of various vertically oriented layers and/or compositions and being quantitatively described by length and width dimensions, sample system feature size, thickness, and optical constants for vertical layer(s)), in identifiably separate laterally disposed regions of said sample system being simultaneously investigated.

It is yet still another purpose of the present invention to identify partially depolarizing sample systems as being comprised of various regions which can be of stepped or gradual geometric shape, can comprise vertically graded layers, can be isotropic or anisotropic, and can be depolarizing or non-depolarizing. That is, there are essentially no limitations placed on sample system structure.

It is still yet another purpose of the present invention to identify use of an ellipsometer system, which can be of any type, (eg. rotating element or modulation element ellipsometer, such as briefly described in the Background Section of this Disclosure), to provide a singly, partially or multiply, polarized beam of electromagnetic radiation, typically of spectroscopic wavelength content, which beam of electromagnetic radiation is caused to impinge upon said patterned sample system, in use, at desired angle(s) of incidence, such that a desired electromagnetic beam spot size is achieved on said patterned sample system, such that an intended number of laterally offset regions are included therewithin where said electromagnetic beam impinges upon said patterned sample system. In some cases the sample system can also be caused to assume different orientations, such as by rotation.

It is another purpose of the present invention to describe the causing of an electromagnetic beam to interact with said patterned sample system which is caused to rotate during during acquisition of ellipsometric data.

It is still yet another purpose of the present invention to teach that purely incoherent addition of electric fields can accurately account for intensity at a detector of an ellipsometer system utilized to investigate a sample system which comprises a plurality of separately identifiably laterally disposed regions which are simultaneously within an electromagnetic beam spot size.

It is yet still another purpose of the present invention to note that the J. A. Woollam Co. WVASE program presently allows regression onto up to ten identifiably separate laterally disposed, (ie. offset with respect to one another), regions in a patterned sample system, each of which regions is modeled as a vertical sequence of layers.

BRIEF DESCRIPTION OF THE DRAWINGS

FIGS. 7a and 7b show Thickness and PSI and DELTA values obtained when an investigating polarized ellipsometer electromagnetic beam is caused to impinge upon said sample system entirely in the region of a sample system which has only native oxide present thereupon.

FIGS. 8a and 8b show similar results to those in FIGS. 7a and 7b where an investigating polarized ellipsometer electromagnetic beam is caused to impinge upon said sample system entirely in the region which has one-hundred (100) nanometers of SiO2 present in addition to the native oxide.

FIGS. 9a and 9b show Thickness and PSI and DELTA values for said sample system where a polarized ellipsometer electromagnetic beam is caused to simultaneously impinge upon separately identifiable laterally disposed regions which have only native oxide present thereupon, and which have one-hundred (100) nanometers of SiO2 present in addition to the native oxide, respectively.

FIG. 9c and 9d shows the percent of polarized electromagnetic beam depolarization resulting in the case of simultaneous investigation of two separately identifiable laterally disposed regions which have only native oxide present thereupon, and which have one-hundred (100) nanometers of SiO2 present in addition to the native oxide, respectively.

FIG. 10a shows a sample system comprising a transparent substrate and a polished back side, (eg. a microscope slide).

FIG. 10b shows the index of refraction for the sample system of FIG. 10a over a spectroscopic range.

FIG. 10c shows the percentage of Depolarization of said polarized ellipsometer electromagnetic beam resulting from backside reflections.

FIG. 10d shows PSI and DELTA values obtained from experimental investigation of a microscope slide of FIG. 10a.

FIG. 10e shows Transmission data obtained from experimental investigation of a microscope slide of FIG. 10a.

DETAILED DESCRIPTION

Figure 1A:
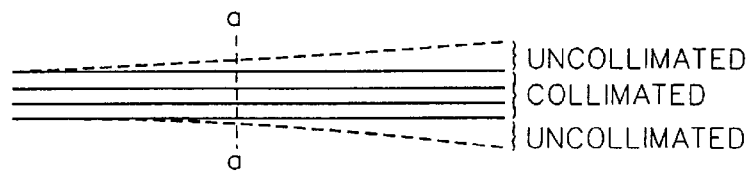
FIG. 1a shows a representation of a collimated electromagnetic beam, with indication of uncollimated components, (eg. an angular bandwidth).

In the Disclosure of the Invention Section of this Specification, it was stated that the present invention identifies characterizing representative parameters which quantitatively describe various aspects of electromagnetic beams. It was stated that the present invention models beams of electromagnetic radiation with certain characterizing representative parameters which serve to describe:

an angular bandwidth (ie. degree of collimation) content,
a degree of temporal and/or a spacial coherence,
a wavelength bandwidth content, and
a partitioning factor which describes how much thereof is described by electric fields which add coherently and how much thereof is described by electric fields which add incoherently to produce an intensity.

In addition, it is to be understood that ellipsometer and polarimeter systems which provide an electromagnetic beam which is utilized in investigating a sample system, can allow setting parameters such as:

angle of incidence an electromagnetic beam makes with respect to the surface of a sample system under investigation;

a "spot size" of an electromagnetic beam at the point where it impinges upon a sample system;

the orientation of a sample system during data acquisition, including stepped sample system rotation and a constantly rotating sample system. (Note, a constantly rotating sample system provides a modulated intensity signal which has relation to an overall effective pattern "aspect ratio").

It is further noted that patterned sample systems can comprise:

separately identifiable laterally disposed regions, each of which has associated therewith effective "width" and "length" dimensions and vertical "height" composition and geometry, and under investigation, one or more separately identifiable laterally disposed region(s) can "shadow" other separately identifiable laterally disposed region(s), and backside reflections in vertically multilayered sample systems can occur.

It is further noted that ellipsometry generally involves obtaining experimental Spectroscopic data for a typically singly polarized electromagentic beam which results after being caused to interact with a sample system at one or more angles of incidence thereto. Typically, data which overdetermines characteristic representative parameters associated with the ellipsometer system, electromagnetic beam and sample system is acquired, and then a square error reducing mathematical regression procedure is practiced with the result being that values for selected characteristic representative parameters are provided along with confidence determining values therefore.

It is further to be understood that data obtained from application of an ellipsometer system in investigation of a sample system, can be utilized in conjunction with a model of said sample system and ellipsometer system in combination, or the effects of said ellipsometer system can be removed from obtained data and the data which results can be utilized in conjunction with a model of the investigated sample system per se. The later case, in effect, obtains data which show how a polarization state of a beam of electromagnetic radiation changes when it interacts with a sample system per se. (That is, the type of ellipsometer becomes irrelevant and only change in polarization state of a beam of electromagnetic radiation which is caused by interaction with a sample system per se. remains relevant). Either approach can provide sample system defining optical and physical parameters, (eg. thickness of layers in various separately identifiable laterally disposed regions, and refractive indicies thereof etc.), with the primary difference being that where the effects of ellipsometer system components remains, analysis of experimentally obtained data requires that a mathematical model must include characteristic parameters of said ellisometer system components, and where the effects of an ellipsometer system have been removed, said mathematical model need only include characteristic parameters for said electromagnetic beam and said sample system per se.

For the purposes of the present invention it is conceptually of benefit to consider that data experimentally obtained utilizing an ellipsometer system have had the ellipsometer system specific effects removed therefrom, as this makes it clear that the present invention is applicable to use with any ellipsometer system, and that it is only a sample system per se. which is being characterized by a change in a beam of singly or multiply polarized, or partially depolarized electromagnetic radiation.

Figure 1B:
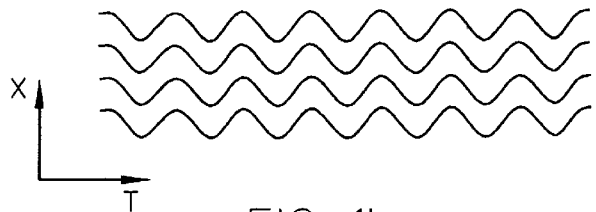
FIG. 1b shows a spacially and temporally coherent waveform.
Figure 1C:
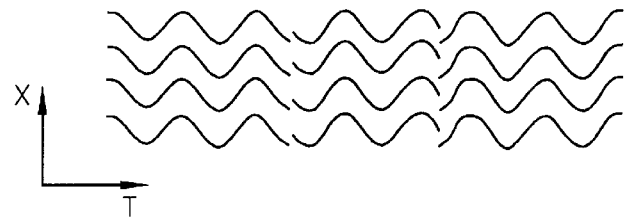
FIGS. 1c and 1d show, respectively a temporally incoherent but spacially coherent waveform, and a temporally and spacially incoherent waveform.
Figure 1D:
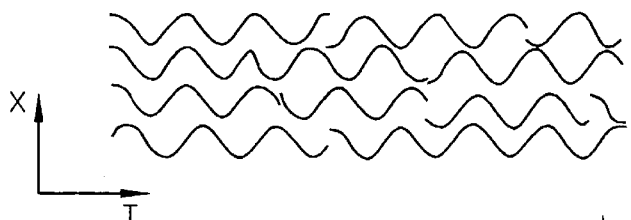
Figure 1E:
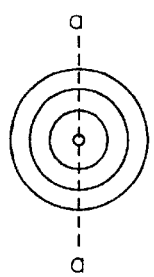
FIG. 1e shows a cross-section of the electromagnetic beam of FIG. 1a taken at a—a, and indicates that the "spot-size" thereof can be controlled, as for instance, by a variable aperture.
Figure 1F:
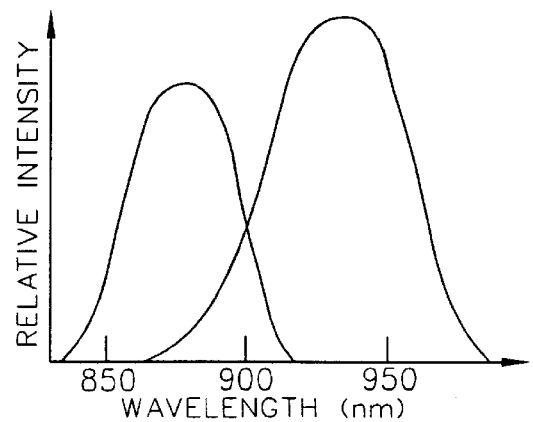
FIG. 1f demonstrates that beams of electromagnetic radiation, even if described as consisting of a specific wavelength, are actually always comprised of a spectrum of wavelengths around some central wavelength.

Turning now to the Figures, there is shown in FIG. 1a, a representation of a collimated electromagnetic beam, with indication of uncollimated components, (eg. an angular bandwidth). It should be easily visualized that an imperfectly collimated beam of electromagnetic radiation impinges upon a sample system at a variety of angles of incidence where a single angle of incidence is intended. FIG. 1b shows a spacially and temporally coherent waveform, and FIGS. 1c and 1d show, respectively a temporally incoherent but spacially coherent waveform, and a temporally and spacially incoherent waveform. FIG. 1e shows a cross-section of the electromagnetic beam of FIG. 1a taken at a—a, and indicates that the "spot-size" thereof can be controlled, as for instance, by a variable aperture. FIG. 1f demonstrates that beams of electromagnetic radiation, even if described as consisting of a specific wavelength, are actually always comprised of a spectrum of wavelengths around some central wavelength.

Figure 2:
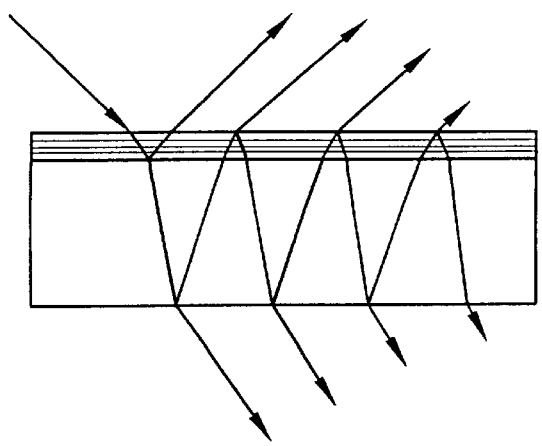
FIG. 2 shows a representation as to how layers in a sample system can cause backside reflections.

FIG. 2 shows a representation as to how layers in a sample system can cause backside reflections. It is noted that if said layer is not too deep, said backside reflection electric fields can add coherently with front-side reflection electric fields. However, relatively deep layers lead to incoherent electric field addition effects.

Figure 3:
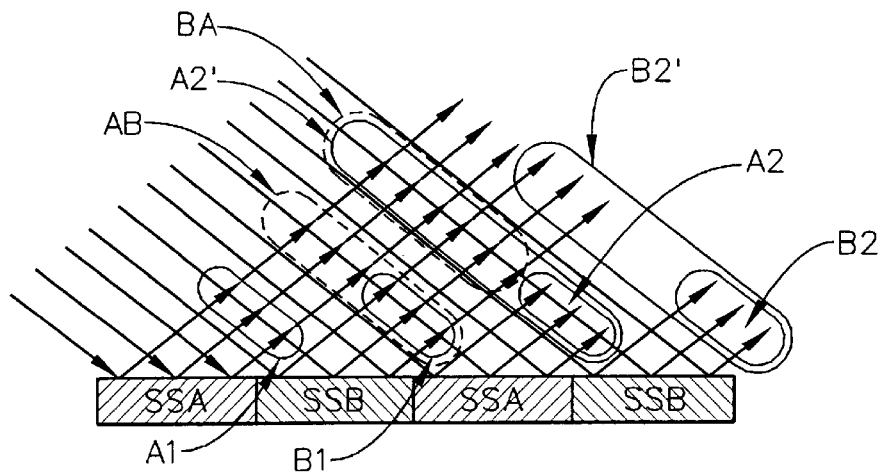
FIG. 3 demonstrates a sample system with four alternating regions present.

FIG. 3 demonstrates a sample system with four alternating regions present. Two regions of a material "SSA" are shown interspersed with two regions of a material "SSB". Beam portions reflecting entirely from a region of a single type (ie. "SSA" or "SSB"), add coherently with one another, (see wavefronts identified as A1, A2 and B1, B2 and B2'), while beam portions reflecting from regions of different types add incoherently, (see wavefronts identified as "AB" and "BA"). It should be appreciated that a partitioned part of a beam reflecting off of the sample system shown in FIG. 3 partially allows for coherent addition of electric fields and that a complimentary partitioned part of a beam reflecting off of the sample system shown in FIG. 3 is partially allows for incoherent addition of electric fields.

Figure 4:
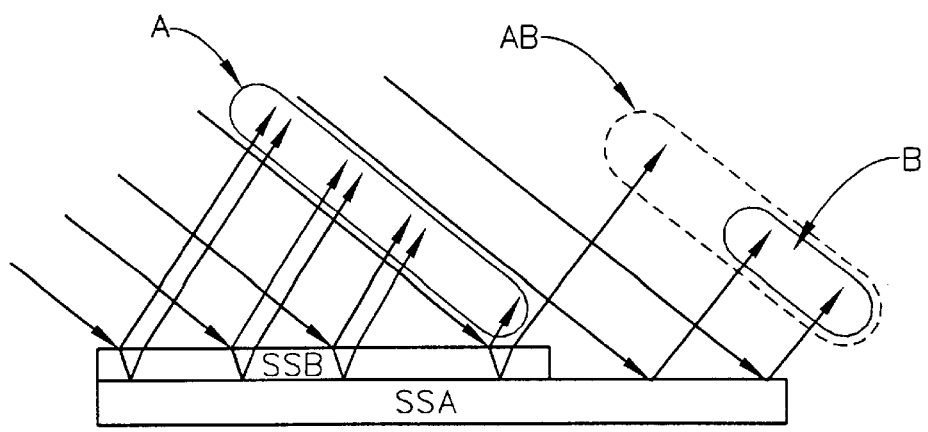
FIG. 4 demonstrates a sample system which is stepped vertically over a portion thereof.

FIG. 4 demonstrates a sample system "SSA" which is stepped vertically "SSB" over a portion thereof. Wavefronts "A" will add coherently, as will wavefronts "B". But note that wavefronts group identified as "AB" might not add coherently.

Figure 5A:
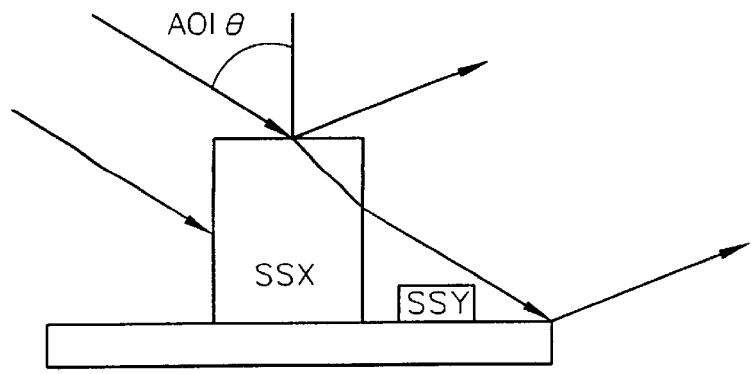
FIG. 5a demonstrates a "shadowing" effect.

FIG. 5a shows that where a sample system has present a plurality of laterally disposed regions (SSX) and (SSY), and an electromagnetic beam impinges thereupon at an angle of incidence (Θ), shadowing effects can occur such that (SSY) is not directly "seen" by said electromagnetic beam.

Figure 5B:
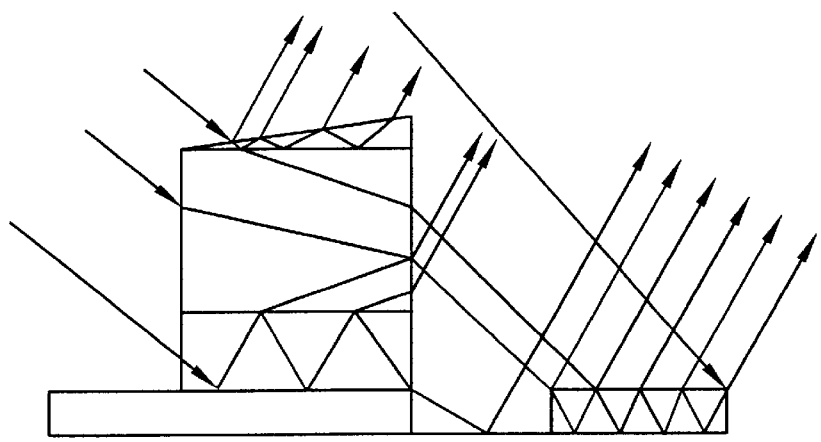
FIG. 5b generally shows relatively complex patterned sample system.

FIG. 5b generally shows that the situation can become very complex where multiple separately identifiable laterally disposed regions are present, each of which present with different vertically oriented layers and composition etc. This is particularly true as backside reflections are present. In such very complex situation, intensity measured by a detector system is the simultaneously the result of partially coherent and partially incoherent addition of electric fields. The present invention teaches that both effects must be simultaneously accounted for in a mathematical model of an electromagentic beam.

Figure 6:
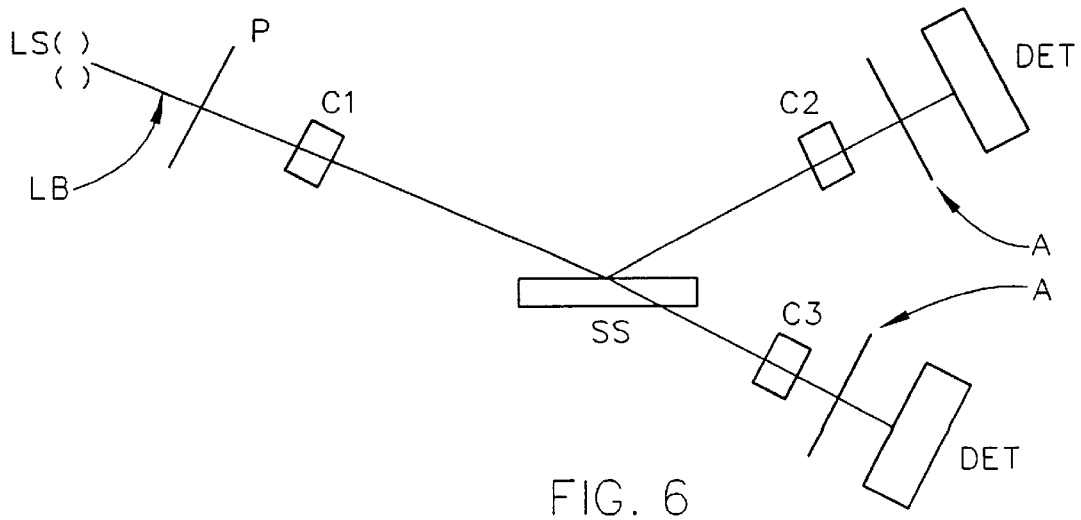
FIG. 6 demonstrates certain reflection and transmission mode ellipsometer systems.

FIG. 6 shows a demonstrative configuration of certain reflection and transmission ellipsometer system configurations. Shown is a source (LS) of a beam of electromagnetic radiation (LB), a polarizer (P), compensators (C1) (C2) (C3), a sample system (SS), and analyzers (A). In use a beam of electromagnetic radiation (LB) is provided by said light source (LS) and passes through said polarizer (P), which serves to set a magnitude of a ratio of "P" and "S" components of said polarized electromagnetic beam of radiation. If present, compensator (C1) serves to set a, phase angle between said "P" and "S" components in said polarized beam electromagnetic beam of radiation, prior to interaction of said polarized beam electromagnetic beam of radiation with said sample system (SS). After interaction of said beam polarized beam electromagnetic beam of radiation with said sample system (SS) it passes through a compensator (C2) or (C3) if present, and then through said analyzer (A) prior to entering said detector (DET) for measurement of the intensity thereof. (And as mentioned infra herein, where a compensator is present in an ellipsometer system, an electromagnetic beam Percent Depolarization parameter can be determined). It is to be understood that other types of ellipsometer systems could equally well be utilized.

It is further to be understood that intensity data obtained by an ellipsometer system often mediates determination of intermediate parameter values, which them must be subjected to, for instance, transfer function or regression, to arrive at sample system representing PSI and DELTA parameter values. In the case of rotating analyzer of rotating polarizer, for instance, parameters conventionally termed ALPHA and BETA are evaluated and then, via transfer functions, are converted to PSI and DELTA. For example:

$$\text{Tan}(\psi) = \frac{\sqrt{1+\alpha}\ \text{ABS}(\text{Tan}P)}{\sqrt{1-\alpha}}$$

$$\text{Cos}(\Delta) = \frac{B}{\sqrt{1-\alpha^2}}$$

With appropriate mathematical attention, the present invention allows working with said intermediate ALPHA and BETA parameter values, or with PSI and DELTA values.

Turning now to FIGS. 7a, 7b, 8a, 8b, 9a, 9b, 9c and 9d there are shown experimental results from investigation of a silicon sample system which has two separately identifiable laterally disposed regions present thereon. One said separately identifiable laterally disposed region being a nominal one-hundred (100) nanometers of $SiO_2$ atop native $SiO_2$, and a second separately identifiable laterally disposed surrounding region being only native $SiO_2$ present. FIGS. 7a and 7b show Thickness and PSI and DELTA values obtained when an investigating polarized ellipsometer electromagnetic beam is caused to impinge upon said sample system entirely in the region which has only a native $SiO_2$ oxide present, and FIGS. 8a and 8b show similar results where an investigating polarized ellipsometer electromagnetic beam is caused to impinge upon said sample system entirely in the region which has an additional nominal one-hundred (100) nanometers of $SiO_2$ present in addition to the native $SiO_2$ oxide. In modeling and analysis, for the cases shown by FIGS. 7a, 7b, 8a and 8b, purely coherent electric field addition was assumed. FIGS. 9a and 9b show Thickness and PSI and DELTA values for said sample system where a polarized ellipsometer electromagnetic beam is caused to simultaneously impinge upon both of the separately identifiable laterally disposed regions, and in modeling and analysis for said case, purely incoherent electric field addition was assumed. FIGS. 9c and 9d show the percent of polarized electromagnetic beam depolarization resulting. The very important thing to note is that FIGS. 8a and 9a provide essentially equivalent $SiO_2$ thickness results, and that FIG. 7a provides essentially equivalent native $SiO_2$ oxide thickness to that in FIGS. 8a and 9a. That is, the fact that the polarized ellipsometer electromagnetic beam simultaneously impinged upon only one, or on two different separately identifiable laterally disposed region did not effect the ability to identify the oxide thicknesses where appropriate, electric field addition criteria was assumed (ie. coherent in FIGS. 7a, 7b, 8a, and 8b cases or incoherent in FIGS. 9a and 9b), emphasis added. What occurred when two separately identifiable laterally disposed regions were simultaneously investigated, was that the polarized ellipsometer electromagnetic beam became partially depolarized. (It is to be noted that assumption of coherent addition of electric fields did not provide accurate thickness and optical constant results where the polarized ellipsometer electromagnetic beam simultaneously impinged two different separately identifiable laterally disposed regions).

It is noted that a retarder element was utilized in data acquisition which appears in FIGS. 9a and 9b, thereby allowing calculation of the Percent Depolarization. For general insight, it is disclosed that:

% depolarization=$(1-\alpha^2-\beta^2-\delta^2)$;

where:

$\alpha$=cos (2 $\psi$);

$\beta = \sin(2\psi)\cos(\Delta)$; and $\delta = \sin(2\psi)\sin(\Delta)$.

While without a retarder element present, $\text{TAN}(\psi)$ and $\text{COS}(\Delta)$ can be found, with a retarder element present, both $\text{SIN}(\Delta)$ and $\text{COS}(\Delta)$ can be found, and beam depolarization is defined to occur where $\text{COS}^2(\Delta) + \text{SIN}^2(\Delta)$ is not equal to 1.0. The reason adding a retarder allows determining both $\text{COS}(\Delta)$ and $\text{SIN}(\Delta)$ is that the "Handedness" of a polarized beam can be determined when a retarder is present, and this allows determining if an angle is in a range of zero (0.0) to one-hundred-eighty (180) degrees, or in a range of one-hundred-eighty (180) degrees to three-hundred-sixty (360) degrees. In effect, the presence of a retarder allows determining if an angle is, for instance +X or −X degrees, where the SIN Function returns opposite sign values. (The COS function returns the same sign value for +X and −X angles, hence can not distinguish between them).

FIGS. 9c and 10c show that a polarized ellipsometer electromagnetic beam can become partially depolarized by simultaneous interaction with separately identifiable laterally disposed regions of a sample system, and by interaction which vertically oriented composition, (eg. layers), which effect front-side and backside reflections.

Figure 10D:
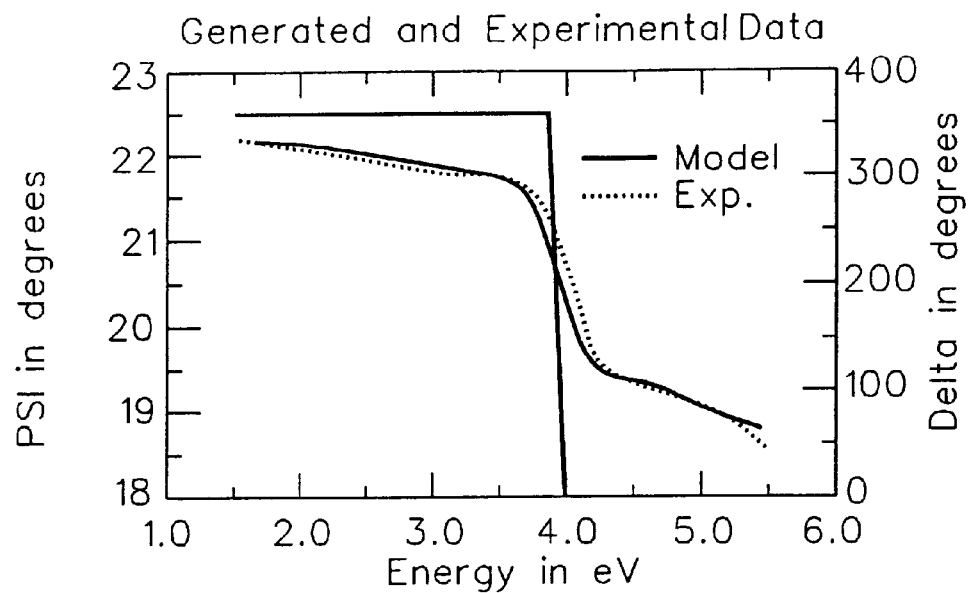
Figure 10E:
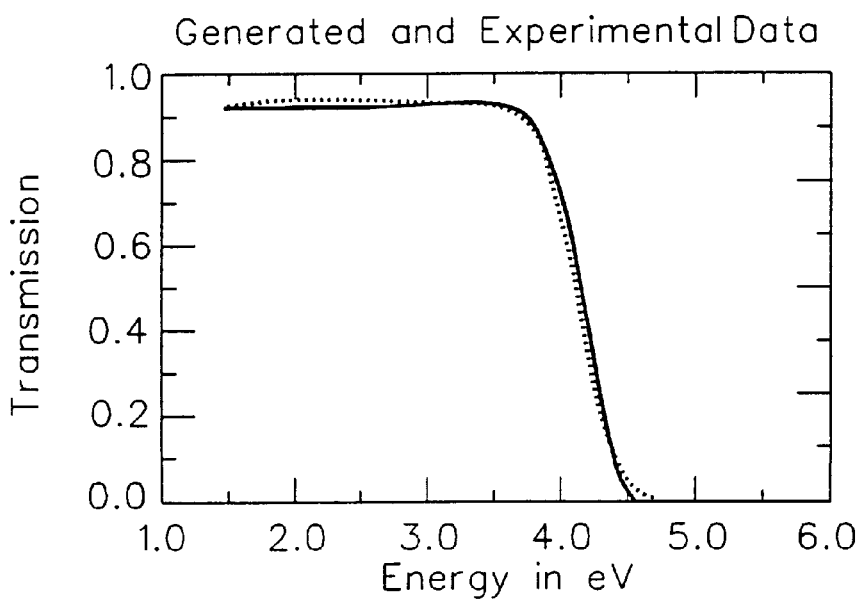

FIGS. 10a10d demonstrate electromagnetic beam depolarizing effects of sample system "backside" reflections. FIG. 10a shows a sample system comprising a transparent substrate with a polished backside, (eg. a microscope slide). A polarized ellipsometer electromagnetic beam interacting with such a sample system will result in a portion thereof being reflected from the top surface and a portion thereof being reflected from the back surface thereof into a detector system. FIG. 10b shows the index of refraction and extinction coefficient for the sample system shown in FIG. 10a over a spectroscopic range. FIG. 10d shows PSI and DELTA values obtained from experimental investigation of a microscope slide, while FIG. 10c shows the percentage of Depolarization of said polarized ellipsometer electromagnetic beam resulting from backside reflections, and FIG. 10e shows Transmission data. It can be considered that all electromagnetic beam reflection from a front surface is coherent, and that all electromagnetic beam reflection from a back surface is coherent, but that electromagnetic beam reflected from the front surface is incoherent with that reflected from the back surface. Thus the total reflected electromagnetic beam is partitioned into two parts. The important thing to note is that backside reflections in the case shown effected a two-and-seven-tenths (2.7%) percent depolarization of an impinging polarized ellipsometer electromagnetic beam, and that to account for said effect the partitioned parts of the electromagentic beam have to be considered to add together incoherently.

It is also noted that the term "polarized" as used in the Claims to describe a beam of electromagnetic radiation is not to be taken to mean purely singly polarized. As appropriate, said term "polarized" is to be interpreted to mean "singly, multiply or partially polarized" states, and is exclusive of only "completely randomly polarized or unpolarized", states.

In conclusion, the present invention teaches that intensity data associated with a beam of electromagentic radiation which has been caused to interact with a patterned sample, must be modeled as resulting from, at least partially, the incoherrent addition of electric fields, and identifies as a relevant electromagentic beam mathematical model parameter, a "partitioning parameter" which defines what percentage of an electromagentic beam intensity is attributable to coherent addition of electric fields and what percentage of an electromagentic beam intensity is attributable to incoherent addition of electric fields. As well, the present invention identifies as relevant electromagentic beam mathematical model parameters an angular bandwidth (ie. degree of collimation) content, a degree of temporal and/or a spacial coherence, and a wavelength bandwidth content. The present invention also includes the possibility of rotating a patterned sample system during experimental data acquisition, and the controlling of an electromagentic beam spot size where it impinges upon a patterned sample system, so as to include varying numbers of separately identifiable laterally disposed regions therewithin. The present invention teaches that identified electromagnetic beam mathematical model parameters are appropriately considered along with optical and physical parameters of separately identifiable laterally disposed regions, each of which has associated therewith effective "width" and "length" dimensions and vertical "height" composition and geometry.

The present invention primarily teaches then, that where a patterned sample system is ellipsometrically investigated, the assumption that experimentally obtained ellipsometric intensity data is the result of purely coherent addition of electric fields (which assumption is conventional practice), is not valid. The present invention teaches that an assumption that partial, or even total, incoherent addition of electric fields in an electromagnetic beam which enters an ellipsometer detector system, after interaction with said patterned sample system, is responsible for producing experimentally obtained ellipsometric intensity data, and that the source of said incoherent electric field addition effects must be included in a mathematical model of said electromagnetic beam, said patterned sample system, (and ellipsometer system), to allow obtaining correct, (regression mediated, for instance), values for optical constants and physical parameters for various separately identifiable laterally disposed regions on an investigated patterned sample system. The present invention also considers that a source electromagentic beam can be singly, partially or multiply polarized. Finally, the foregoing has served to identify many examples of the source of electromagnetic beam depolarizing effects, which depolarization effects, in many cases, necessitate application of: a mathematical model which includes characteristic parameters which are relevant because of a valid assumption that experimentally measured ellipsometric intensity values result from other than purely coherent addition of electric fields.

Finally, it is noted that ellipsometer and polarimeter systems monitor polarization state of electromagnetic radiation, where polarization state comprises a ratio of orthogonal components, a phase angle between said orthogonal components. Said monitoring is typically mediated by a detector system which measures an intensity, analysis of which provides insight into polarization state. This use of the term "intensity" is to be distinguished from that encountered in the practice of reflectometry wherein polarization state is not of concern.

Having hereby disclosed the subject matter of the present invention, it should be apparent that many modifications, substitutions, and variations of the present invention are possible in light thereof. It is to be understood that the present invention can be practiced other than as specifically described and should be limited in scope and breadth only by the appended Claims.

We claim:

1. A method of investigating a partially polarized electromagnetic beam comprising the steps of:

a. selecting representative parameters of an electromagnetic beam from the group consisting of:
   a degree of temporal coherence;
   a degree of spacial coherence;
   a wavelength bandwidth content; and
   a degree of collimation determining angular bandwidth;
b. causing a polarized electromagnetic beam to interact with a sample system comprising a plurality of laterally disposed regions, with a resulting specular zeroth-order of said polarized electromagnetic beam which results from said interaction, being caused to enter a detector system that intensity data is experimentally obtained;
c. proposing a mathematical model for the specular zeroth-order electromagnetic beam and sample system, in which mathematical model said specular zeroth-order electromagnetic beam is considered as partitioned into first and second parts, and such that said obtained intensity data is considered to be the result of simultaneous partially coherent:

$$(E1+E2+\ldots En)*(E1+E2+\ldots +En)*$$

and partially incoherent:

$$E1*E1*)+(E2*E2*)+\ldots +(En*En*)$$

addition of electric field components, respectively, in said first and second partitioned parts of said specular zeroth-order electromagnetic beam, which mathematical model further comprises characterizing parameters representative of at least some of said plurality of laterally disposed regions; and e. evaluating selected representative parameter(s) which characterize said specular zeroth-order electromagnetic beam and at least two of said plurality of laterally disposed regions in said mathematical model of said sample system, utilizing said experimentally obtained intensity data.

2. A method of investigating a partially polarized electromagnetic beam as in claim 1, in which the step of proposing a mathematical model for the specular zeroth-order electromagnetic beam and sample system, includes accounting for at least one selection from the group consisting of:
   effects of lateral and vertical dimensions of at least one of said plurality of laterally disposed regions; and effects of back-side reflections caused by interfacing between vertically nonhomogeneous layers in at least one of said plurality of laterally disposed regions.

3. A method of sample system investigation involving a partially polarized beam of electromagnetic radiation, comprising the steps of:
a. providing an ellipsometer system comprising means for causing a polarized beam of electromagnetic radiation selected from the group consisting of:
   singly;
   partially, and
   multiply polarized;
to interact with a sample system and enter means for detecting a resulting beam of electromagnetic radiation after said interaction with said sample system;
b. placing a sample system which comprises a plurality of laterally disposed regions into said ellipsometer system;

c. causing a polarized beam of electromagnetic radiation to interact with said sample system such that a resulting specular zeroth-order thereof, which results from said interaction, is caused to enter said means for detecting said polarized beam, such that specular zeroth-order electromagnetic beam and sample system characterizing ellipsometer intensity data is experimentally obtained;
d. proposing a mathematical model for the specular zeroth-order beam of electromagnetic radiation and sample system, in which mathematical model said specular zeroth-order beam of electromagnetic radiation, present after interaction of said polarized electromagnetic beam with said sample system, is considered as partitioned into first and second parts, and such that said obtained ellipsometric intensity data is modeled as being the result of coherent:

$$(E1+E2+\ldots En)*(E1+E2+\ldots +En)*$$

and incoherent:

$$[(E1*E1*)+(E2*E2*)+\ldots +(En*En)]$$

addition of electric field components, respectively, in said first and second partitioned parts of said specular zeroth-order electromagnetic beam present after interaction of said polarized electromagnetic beam of radiation with said plurality of laterally disposed regions in said sample system, which mathematical model further comprises characterizing parameters representative of at least some of said plurality of laterally disposed regions; and e. evaluating characterizing parameter(s) representative of at least one of said plurality of laterally disposed regions in said mathematical model of said sample system, utilizing said experimentally obtained intensity data.

4. A method of investigating sample systems in ellipsometer systems as in claim 3, which further comprises the step of identifying the relative relationship of wavelength to laterally disposed regions dimensions content of the polarized beam of electromagnetic radiation and allocating a greater portion of said specular zeroth-order beam of electromagnetic radiation to said first partitioned part thereof, which involves coherent electric field component addition, as the wavelength(s) present, relative to said laterally disposed regions dimensions therein become longer; and allocating a greater portion of said specular zeroth-order beam of electromagnetic radiation to said second partitioned part of said specular zeroth-order beam of electromagnetic radiation, which involves incoherent electric field component addition, as the wavelength(s) present, relative to said laterally disposed regions dimensions therein become shorter.

5. A method of investigating sample systems in ellipsometer systems as in claim 4, which further includes the step of controlling the wavelength content of the polarized electromagnetic beam and:
   as the wavelength(s) present therein become longer than the laterally disposed regions dimensions content, allocating a greater portion of said zeroth-order beam of electromagnetic radiation to said first partitioned part thereof, which involves coherent electric field component addition; and
   as the wavelength(s) present therein become shorter than the laterally disposed regions dimensions content, allocating a greater portion of said zeroth-order beam of electromagnetic radiation to said second partitioned part of said zeroth-order beam of electromagnetic radiation, which involves incoherent electric field component addition;

such that a majority of said zeroth-order beam of electromagnetic beam is allocated to said first partitioned part when said wavelength(s) present are much larger than dimensions of laterally disposed regions of said sample system, and such that a majority of said zeroth-order beam of electromagnetic radiation is allocated to said second partitioned part when said wavelength(s) present are much smaller than dimensions of laterally disposed regions of said sample system.

6. A method of investigating sample systems in ellipsometer systems as in claims 3, 4 and 5 which further comprises the step of controlling the spot size of the polarized electromagnetic beam where it is caused to impinge upon and interact with said sample system, so as to control the number of laterally disposed regions present on said sample system which are therewithin.

7. A method of investigating sample systems in ellipsometer systems as in claim 3, in which said mathematical model for said zeroth-order beam of electromagnetic radiation includes characterizing representative parameters selected from the group consisting of:

a degree of temporal coherence;
a degree of spacial coherence;
a wavelength bandwidth content; and
a degree of collimation determining angular bandwidth.

8. A method of investigating sample systems in ellipsometer systems as in claim 3, in which said mathematical model for said sample system includes characterizing representative parameters selected from the group consisting of:

length/and width dimensions, size, thickness and optical constants for vertical layer(s);

in laterally disposed regions of said sample system being simultaneously investigated.

9. A generalized method of simultaneously investigating a plurality of regions in a patterned sample system utilizing ellipsometry, comprising the steps of:

a. providing a sample system which comprises a plurality of identifiably separate laterally offset regions, each of said identifiably separate laterally offset regions being comprised of vertically oriented layer(s) and/or composition(s), said identifiably separate laterally offset regions each being of length and width dimensions varying from sub-micron and below to hundreds of microns and larger in various directions, each of said identifiably separate laterally offset regions containing at least one layer which is of a side elevational geometrical shape selected from the group consisting of:

step and gradual; and of a vertically directed composition selected from the group consisting of:

homogeneous and graded;

each said identifiably separate laterally offset region having properties selected from the group consisting of:

isotropic;
anisotropic;
depolarizing; and
non-depolarizing;

b. providing an ellipsometer system capable of providing a beam of electromagnetic radiation with a polarization state selected from the group consisting of:

singly;
partially; and
multiply polarized;

said beam of electromagnetic radiation being characterized by:

degree(s) of temporal coherence;
degree(s) of spacial coherence;
wavelength bandwidth content; and
degree of collimation determining angular bandwidth;

c. causing said beam of electromagnetic radiation to impinge upon said patterned sample system at at least one desired angle(s) of incidence, such that for each angle of incidence a desired electromagnetic beam spot size is achieved on said patterned sample system such that an intended number of identifiably separate laterally offset regions are included therewithin where said beam of electromagnetic radiation impinges upon said patterned sample system; a specular zeroth-order beam of electromagnetic radiation formed after interaction with said patterned sample system, being caused to enter a detector system in said ellipsometer system;

d. providing a mathematical model of said ellipsometer system in combination with said patterned sample system, said mathematical model including representative characterizing parameters selected from the group consisting of:

for vertical layer(s) in identifiably separate laterally offset regions of said patterned sample system being simultaneously investigated:

length and width, thickness(es) and optical constants, and for said beam of electromagnetic radiation:

degree(s) of temporal coherence and degree(s) of spacial coherence, and a wavelength bandwidth content, and a degree of collimation determining angular bandwidth, and electromagnetic beam partition coefficient(s) which identify what percentage of an intensity associated with said electromagnetic beam is the result of coherent addition of electric field components and what percentage is the result of incoherent addition of electric field components, and for effects of layer interface and back-side reflections in identifiably separate laterally offset region;

e. performing a simultaneous regression of all selected model representative characterizing parameters onto experimentally obtained detector provided intensity data to determine if the proposed model, with least square error reducing adjustments to initially proposed variables introduced, accounts for the experimental data in all simultaneously investigated identifiably separate laterally offset regions.

10. A generalized method of simultaneously investigating a plurality of regions in a patterned sample system utilizing ellipsometry as in claim 9, in which the step of providing a mathematical model includes a selection from the group consisting of:

providing a mathematical model which bases intensity calculations primarily on an approach which handles signals which result from addition of parts of said beam of electromagnetic radiation which interact with identifiably separate laterally offset pattern regions as resulting from "choherent" addition, in that parts of said beam of electromagnetic radiation which travel one spacial pathway have a phase relationship to parts of said beam of electromagnetic radiation which travel an alternative spacial pathway, thereby possibly entering interference effects into production of an intensity signal and requiring that intensity be calculated by:

$I=(E1+E2+\ldots En)^*(E1+E2+\ldots +En)^*$; and providing a mathematical model which bases intensity calculations primarily on an approach which handles signals which result from addition of parts of said beam of electromagnetic radiation which interact with identifiably separate laterally offset pattern regions as resulting from "incoherent" addition, in that parts of said beam of electromagnetic radiation which travel one spacial pathway have a lack of phase relationship to parts of said beam of electromagnetic radiation which travel an alternative spacial pathway, such that phase relationships between them are essentially negligible and require that intensity be calculated by:

$I=[(E1^*E1^*)+(E2^*E2^*)+\ldots +(En^*En^*)]$;

and providing a mathematical model which bases intensity calculations on an approach which handles signals which result from addition of parts of said beam of electromagnetic radiation which interact with identifiably separate laterally offset pattern regions as resulting from partially "coherent" and partially "incoherent" addition of electric field components, thereby requiring simultaneous utilization of intensity determining calculations based upon both:

$I=(E1+E2+\ldots En)^*(E1+E2+\ldots +En)^*$, and $I=[(E1^*E1^*)+(E2^*E2^*)+\ldots +(En^*En^*)]$.

11. A method of sample system investigation involving a partially polarized beam of electromagnetic radiation, comprising the steps of:
   a. providing an ellipsometer system comprising means for causing a polarized beam of electromagnetic radiation selected from the group consisting of:
   singly;
   partially; and
   multiply polarized;
to interact with a sample system and enter means for detecting a resulting beam of electromagnetic radiation after said interaction with said sample system, said ellipsometer system including means for controlling angle of incidence to a sample system surface, the wavelength content, and spot size of the polarized electromagnetic beam where it is caused to impinge upon and interact with said sample system, so as to control the polarized electromagnetic beam area and hence, the number of laterally disposed regions present on said sample system which are therewithin;
   b. placing a sample system which comprises a plurality of laterally disposed regions into said ellipsometer system;
   c. at a plurality electromagnetic beam settings of at least one member of the group consisting of:
   polarized electromagnetic beam:
   angle of incidence to said sample system surface;
   wavelength content; and
   beam spot size;
causing polarized beams of electromagnetic radiation to interact with said sample system such that a resulting specular zeroth-order thereof, which results from said interaction, is caused to enter said means for detecting said polarized beam, such that specular zeroth-order electromagnetic beam and sample system characterizing ellipsometer intensity data is experimentally obtained;
   d. proposing a mathematical model for the specular zeroth-order beam of electromagnetic radiation and sample system, in which mathematical model said specular zeroth-order beam of electromagnetic radiation, present after interaction of said polarized electromagnetic beam with said sample system, is considered as partitioned into first and second parts, and such that said obtained ellipsometric intensity data is assumed to be the result of coherent:

$[(E1+E2+\ldots En)^*(E1+E2+\ldots +En)^*]$ and incoherent:

$[(E1^*E1^*)+(E2^*E2^*)+\ldots +(En^*En^*)]$ addition of electric field components, respectively, in said first and second partitioned parts of said specular zeroth-order electromagnetic beam present after interaction of said polarized electromagnetic beam of radiation with said plurality of laterally disposed regions in said sample system, which mathematical model further comprises characterizing parameters representative of at least some of said plurality of laterally disposed regions;
   e. evaluating characterizing parameter(s) representative of at least one of said plurality of laterally disposed regions in said mathematical model of said sample system, utilizing said experimentally obtained intensity data.

12. A method of sample system investigation involving a partially polarized beam of electromagnetic radiation as in claim 11, in which the step of providing an ellipsometer system includes providing an ellipsometer system with the capability of causing a sample system placed thereinto to assume various rotational orientations of said sample system, and in which the step of causing polarized beams of electromagnetic radiation to interact with said sample at a plurality electromagnetic beam settings of at least one member of the group consisting of:
   polarized electromagnetic beam:
   angle of incidence to said sample system surface;
   wavelength content; and
   beam spot size;
further includes causing said sample system to assume a plurality of rotational orientations; such that a resulting specular zeroth-order thereof, which results from said interaction, is caused to enter said means for detecting said polarized beam, such that specular zeroth-order electromagnetic beam and sample system characterizing ellipsometer intensity data is experimentally obtained for at least two sample system orientations.

13. A method of sample system investigation involving a partially polarized beam of electromagnetic radiation as in claim 12, in which said sample system is caused to continuously rotate during data acquisition and said mathematical model includes provision therefore.

14. A method of sample system investigation involving a partially polarized beam of electromagnetic radiation as in claim 11, in which the step of placing a sample system which comprises a plurality of laterally disposed regions into said ellipsometer system involves selecting a sample system from the group consisting of:

a sample system with a plurality of essentially similar lateral dimension size laterally disposed regions; and a sample system with a plurality of laterally disposed regions of different lateral dimension sizes.

15. A method of sample system investigation involving a partially polarized beam of electromagnetic radiation as in claim 11, in which the step of placing a sample system which comprises a plurality of laterally disposed regions into said ellipsometer system involves selecting a sample system with laterally disposed regions selected from the group consisting of:

a sample system with similar vertically directed dimensions and/or compositions; and a sample system with different vertically directed dimensions and/or compositions.

16. A method of analyzing a polarized electromagnetic beam comprising the steps of:

a. providing a polarized electromagnetic beam;

b. measuring intensity data therefore;

c. providing a mathematical model for said polarized electromagnetic beam based upon a criteria that said intensity data results from incoherent:

$$[(E1^*E1^*)+(E2^*E2^*)+\ldots+(En^*En^*)]$$

addition of electric field components, which mathematical model includes at least one polarized electromagnetic beam characterizing representative parameter selected from the group consisting of:

a wavelength bandwidth content characterizing representative parameter, and a degree of collimation determining angular bandwidth characterizing representative parameter;

d. evaluating at least one partially polarized electromagnetic beam characterizing representative parameter(s) of said mathematical model using said measured intensity data;

in which method of analyzing a polarized electromagnetic beam, the steps of providing a polarized beam of electromagnetic radiation and measuring intensity data therefore involves:

providing an ellipsometer system comprising means for causing a polarized beam of electromagnetic radiation selected from the group consisting of:
singly;
partially; and
multiply polarized;

to interact with a sample system and enter means for detecting a resulting beam of electromagnetic radiation after said interaction with said sample system, said ellipsometer system including means for controlling the wavelength content, and spot size of the polarized electromagnetic beam where it is caused to interact with said sample system, so as to control the polarized electromagnetic beam area and hence, the number of laterally disposed regions present on said sample system which are therewithin;

placing a sample system which comprises a plurality of laterally disposed regions of dimensions larger than the wavelength of said polarized electromagnetic beam into said ellipsometer system;

at at least one of a plurality of settings of at least one member of the group consisting of polarized electromagnetic beam: wavelength content; and
beam spot size;

causing said polarized beam of electromagnetic radiation to interact with said sample system such that a resulting specular zeroth-order thereof, which results from said interaction, is caused to enter said means for detecting said polarized beam, such that specular zeroth-order electromagnetic beam and sample system characterizing ellipsometer intensity data is experimentally obtained, said specular zeroth-order electromagnetic beam and sample system characterizing ellipsometer intensity data comprising said provided polarized electromagnetic beam.

17. A method of analyzing a polarized electromagnetic beam comprising the steps of:

a. providing a polarized electromagnetic beam;

b. measuring intensity data therefore;

c. providing a mathematical model for said polarized electromagnetic beam based upon a criteria that said intensity data results from coherent:

$$(E1+E2+\ldots En)^*(E1+E2+\ldots +En)^*$$

addition of electric field components, which mathematical model includes at least one polarized electromagnetic beam characterizing representative parameter selected from the group consisting of:

a wavelength bandwidth content characterizing representative parameter; and a degree of collimation determining angular bandwidth characterizing representative parameter; and d. evaluating at least one partially polarized electromagnetic: beam characterizing representative parameter(s) of said mathematical model using said measured intensity data;

in which method of analyzing a polarized electromagnetic beam the step of providing a polarized beam of electromagnetic radiation and measuring intensity data therefore involves:

providing an ellipsometer system comprising means for causing a polarized beam of electromagnetic radiation selected from the group consisting of:
singly;
partially; and
multiply polarized;

to interact with a sample system and enter means for detecting a resulting beam of electromagnetic radiation after said interaction with said sample system, said ellipsometer system including means for controlling the wavelength content, and spot size of the polarized electromagnetic beam where it is caused to impinge upon and interact with said sample system, so as to control the polarized electromagnetic beam area and hence, the number of laterally disposed regions present on said sample system which are therewithin;

placing a sample system which comprises a plurality of laterally disposed regions of dimensions smaller than the wavelength of said polarized electromagnetic beam into said ellipsometer system;

at at least one of a plurality of settings of at least one member of the group consisting of polarized electromagnetic beam: wavelength content; and
beam spot size;

causing said polarized beam of electromagnetic radiation to interact with said sample system such that a resulting specular zeroth-order thereof, which results from said interaction, is caused to enter said means for detecting said polarized beam, such that specular zeroth-order electromagnetic beam and sample system characterizing ellipsometer intensity data is experimentally obtained, said specular zeroth-order electromagnetic beam and sample system characterizing ellipsometer intensity data comprising said provided polarized electromagnetic beam.

18. A method of sample system investigation involving a partially polarized beam of electromagnetic radiation as in claims 3, 11, 16 and 17 in which the step of evaluating characterizing parameter(s) representative of at least one of said plurality of laterally disposed regions in said mathematical model of said sample system, utilizing said experimentally obtained intensity data involves use of square error reducing mathematical regression.

* * * * *